US010344106B2

(12) United States Patent
Lief et al.

(10) Patent No.: US 10,344,106 B2
(45) Date of Patent: *Jul. 9, 2019

(54) PROCESS FOR REDUCING THE LIGHT OLIGOMER CONTENT OF POLYPROPYLENE OILS

(71) Applicant: Chevron Phillips Chemical Company LP, The Woodlands, TX (US)

(72) Inventors: Graham R. Lief, Bartlesville, OK (US); Uriah J. Kilgore, Kingwood, TX (US); Eric J. Haschke, Bartlesville, OK (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 5 days.

This patent is subject to a terminal disclaimer.

(21) Appl. No.: 15/915,170

(22) Filed: Mar. 8, 2018

(65) Prior Publication Data

US 2018/0194879 A1 Jul. 12, 2018

Related U.S. Application Data

(63) Continuation of application No. 15/235,145, filed on Aug. 12, 2016, now Pat. No. 9,951,158.

(51) Int. Cl.
| | | |
|---|---|---|
| *C08F 10/06* | (2006.01) | |
| *B01J 31/16* | (2006.01) | |
| *C07C 2/32* | (2006.01) | |
| *C07C 5/03* | (2006.01) | |
| *B01J 21/12* | (2006.01) | |
| *B01J 27/12* | (2006.01) | |
| *B01J 31/14* | (2006.01) | |
| *B01J 31/22* | (2006.01) | |
| *C08F 110/06* | (2006.01) | |
| *C08F 4/659* | (2006.01) | |
| *C08F 4/6592* | (2006.01) | |

(52) U.S. Cl.
CPC .............. *C08F 10/06* (2013.01); *B01J 21/12* (2013.01); *B01J 27/12* (2013.01); *B01J 31/143* (2013.01); *B01J 31/1608* (2013.01); *B01J 31/1616* (2013.01); *B01J 31/1625* (2013.01); *B01J 31/1633* (2013.01); *B01J 31/2295* (2013.01); *C07C 2/32* (2013.01); *C07C 5/03* (2013.01); B01J 2231/20 (2013.01); B01J 2531/0263 (2013.01); B01J 2531/48 (2013.01); B01J 2531/49 (2013.01); C07C 2531/22 (2013.01); C08F 4/65912 (2013.01); C08F 4/65916 (2013.01); C08F 4/65925 (2013.01); C08F 4/65927 (2013.01); C08F 110/06 (2013.01); C08F 2420/02 (2013.01); C08F 2500/04 (2013.01); C08F 2500/17 (2013.01)

(58) Field of Classification Search
CPC ....................................................... C08F 10/06

USPC .......................................................... 585/255
See application file for complete search history.

(56) References Cited

U.S. PATENT DOCUMENTS

| | | | |
|---|---|---|---|
| 3,242,099 A | 3/1966 | Manyik et al. | |
| 4,105,837 A * | 8/1978 | Prosser ..................... | C08F 8/48 |
| | | | 525/339 |
| 4,794,096 A | 12/1988 | Ewen | |
| 4,808,561 A | 2/1989 | Welborn, Jr. | |
| 5,576,259 A | 11/1996 | Hasegawa et al. | |
| 5,807,938 A | 9/1998 | Kaneko et al. | |
| 5,919,983 A | 7/1999 | Rosen | |
| 6,107,230 A | 8/2000 | McDaniel et al. | |
| 6,165,929 A | 12/2000 | McDaniel et al. | |
| 6,291,608 B1 | 9/2001 | Eilerts et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 7,199,073 B2 | 4/2007 | Martin | |
| 7,226,886 B2 | 6/2007 | Jayaratne et al. | |
| 7,294,599 B2 | 11/2007 | Jensen et al. | |
| 7,312,283 B2 | 12/2007 | Martin et al. | |
| 7,601,665 B2 | 10/2009 | McDaniel et al. | |
| 7,619,047 B2 * | 11/2009 | Yang ........................ | C08F 10/00 |
| | | | 502/113 |
| 7,884,163 B2 | 2/2011 | McDaniel et al. | |
| 7,989,670 B2 | 8/2011 | Wu et al. | |
| 8,114,946 B2 | 2/2012 | Yang et al. | |
| 8,207,390 B2 | 6/2012 | Wu et al. | |
| 8,309,485 B2 | 11/2012 | Yang et al. | |
| 8,513,478 B2 | 8/2013 | Wu et al. | |
| 8,530,712 B2 | 9/2013 | Wu et al. | |

(Continued)

OTHER PUBLICATIONS

U.S. Appl. No. 15/297,179, entitled "Process for Reducing the Light Oligomer Content of Polypropylene Oils," filed Oct. 19, 2016.

*Primary Examiner* — Philip Y Louie
*Assistant Examiner* — Aaron W Pierpont
(74) *Attorney, Agent, or Firm* — Merchant & Gould P.C.

(57) ABSTRACT

Disclosed herein are dual catalyst compositions containing an unbridged metallocene compound, a bridged metallocene compound, a chemically-treated solid oxide, and an optional co-catalyst. These catalyst compositions can be used for the oligomerization of propylene to produce an oligomer product. For example, a heavy propylene oligomer can be recovered from the oligomer product, and the heavy propylene oligomer can be characterized by a high flash point and viscosity index, and a low pour point.

20 Claims, No Drawings

(56) References Cited

U.S. PATENT DOCUMENTS

| | | |
|---|---|---|
| 8,623,973 B1 | 1/2014 | McDaniel et al. |
| 8,703,886 B1 | 4/2014 | Yang et al. |
| 8,921,291 B2 | 12/2014 | Wu et al. |
| 9,023,959 B2 | 5/2015 | McDaniel et al. |
| 9,951,158 B2 | 4/2018 | Lief et al. |
| 2010/0317904 A1 | 12/2010 | Small et al. |
| 2014/0088319 A1 | 3/2014 | Tang et al. |
| 2017/0022439 A1 | 1/2017 | Kilgore et al. |
| 2018/0105478 A1 | 4/2018 | Lief et al. |

* cited by examiner

PROCESS FOR REDUCING THE LIGHT OLIGOMER CONTENT OF POLYPROPYLENE OILS

This application is a continuation application of co-pending U.S. patent application Ser. No. 15/235,145, filed on Aug. 12, 2016, now U.S. Pat. No. 9,951,158, the disclosure of which is incorporated herein by reference in its entirety.

BACKGROUND OF THE INVENTION

The present invention relates generally to processes for oligomerizing propylene with a dual metallocene catalyst composition comprising an unbridged metallocene compound, a bridged metallocene compound, a chemically-treated solid oxide, and an optional co-catalyst, and to propylene oligomers having reduced light oligomer content and higher flash points.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Aspects of this invention are directed to a process comprising contacting a catalyst composition with an olefin feedstock comprising propylene to form an oligomer product under oligomerization conditions. The catalyst composition can comprise (i) catalyst component I comprising an unbridged metallocene compound, (ii) catalyst component II comprising a bridged metallocene compound, (iii) a chemically-treated solid oxide, and (iv) optionally, a co-catalyst. A heavy propylene oligomer can be isolated from the oligomer product, and the heavy propylene oligomer can have a reduced amount of light oligomers and an unexpectedly high flash point.

In particular aspects of this invention, the heavy propylene oligomer can be characterized by a flash point in a range from about 140 to about 300° C. (or from about 140 to about 260° C.), a viscosity index in a range from about 75 to about 200 (or from about 80 to about 130), and a pour point in a range from about 0 to about −55° C. (or from about −5 to about −30° C.). The heavy propylene oligomer can be used in base oils, or in lubricants and other compositions.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

While compositions and methods are described herein in terms of "comprising" various components or steps, the compositions and methods can also "consist essentially of" or "consist of" the various components or steps, unless stated otherwise. For example, a catalyst composition consistent with aspects of the present invention can comprise; alternatively, can consist essentially of; or alternatively, can consist of; catalyst component I, catalyst component II, a chemically-treated solid oxide, and optionally, a co-catalyst.

The terms "a," "an," "the," etc., are intended to include plural alternatives, e.g., at least one, unless otherwise specified. For instance, the disclosure of "a chemically-treated solid oxide" or "a bridged metallocene compound" is meant to encompass one, or mixtures or combinations of more than one, chemically-treated solid oxide or bridged metallocene compound, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

The terms "contact product," "contacting," and the like, are used herein to describe compositions and methods wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The terms "oligomerization product" and "oligomer product" include all products made by the "oligomerization" process including the "oligomers" and products which are not "oligomers" (e.g., polymer). As used herein, "heavy propylene oligomer" typically refers to a propylene oligomer (or composition) having little to no light propylene oligomers, e.g., a propylene oligomer (or composition) where at least a portion of lighter oligomers (such as $C_6$, $C_9$, and $C_{12}$ oligomers), if produced, has been removed from the "oligomer product." Thus, term "heavy propylene oligomer" generally refers to a propylene oligomer (or composition) isolated from a process producing an oligomer product. This term also can be used generically herein to include propylene homo-oligomers, propylene co-oligomers, and so forth.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is directed generally to new oligomerization catalyst compositions, methods for preparing the catalyst compositions, methods for using the catalyst compositions to oligomerize olefins, the oligomer products produced using such catalyst compositions, and formulations and other products produced using these oligomer products. In particular, the present invention relates to dual metallocene catalyst compositions, to oligomerization processes utilizing such catalyst compositions to oligomerize propylene, and to the resulting heavy propylene oligomers produced from the oligomerization processes. Beneficially, the dual metallocene catalyst compositions can be used to produce heavy propylene oligomers with higher flash points than can be produced under the same conditions with the respective single metallocene catalyst systems.

Catalyst Component I

Catalyst component I can comprise an unbridged zirconium or hafnium based metallocene compound. In one aspect, for instance, catalyst component I can comprise an unbridged zirconium or hafnium based metallocene compound containing two cyclopentadienyl groups, two indenyl groups, or a cyclopentadienyl and an indenyl group. In another aspect, catalyst component I can comprise an unbridged zirconium or hafnium based metallocene compound containing two cyclopentadienyl groups. In yet another aspect, catalyst component I can comprise an unbridged zirconium or hafnium based metallocene compound containing two indenyl groups. In still another aspect, catalyst component I can comprise an unbridged zirconium or hafnium based metallocene compound containing a cyclopentadienyl and an indenyl group.

In some aspects, catalyst component I can comprise an unbridged zirconium (or hafnium) based metallocene compound containing two cyclopentadienyl groups, two indenyl groups, or a cyclopentadienyl and an indenyl group, wherein catalyst component I is capable of producing atactic polypropylene from propylene monomer.

Catalyst component I can comprise, in particular aspects of this invention, an unbridged metallocene compound having formula (I):

Within formula (I), $M^1$, $Cp^A$, $Cp^B$, and each X are independent elements of the unbridged metallocene compound. Accordingly, the unbridged metallocene compound having formula (I) can be described using any combination of $M^1$, $Cp^A$, $Cp^B$, and X disclosed herein.

Unless otherwise specified, formula (I) above, any other structural formulas disclosed herein, and any metallocene complex, compound, or species disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In accordance with aspects of this invention, the metal in formula (I), $M^1$, can be Zr or Hf. In one aspect, for instance, $M^1$ can be Zr, while in another aspect, $M^1$ can be Hf.

Each X in formula (I) independently can be a monoanionic ligand. In some aspects, suitable monoanionic ligands can include, but are not limited to, H (hydride), $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $-OBR^Z_2$, or $-OSO_2R^Z$, wherein $R^Z$ is a $C_1$ to $C_{36}$ hydrocarbyl group. It is contemplated that each X can be either the same or a different monoanionic ligand.

In one aspect, each X independently can be H, $BH_4$, a halide (e.g., F, Cl, Br, etc.), a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group. Alternatively, each X independently can be H, $BH_4$, a halide, $OBR^Z_2$, or $OSO_2R^Z$, wherein $R^Z$ is a $C_1$ to $C_{18}$ hydrocarbyl group. In another aspect, each X independently can be H, $BH_4$, a halide, a $C_1$ to $C_{12}$ hydrocarbyl group, a $C_1$ to $C_{12}$ hydrocarboxy group, a $C_1$ to $C_{12}$ hydrocarbylaminyl group, a $C_1$ to $C_{12}$ hydrocarbylsilyl group, a $C_1$ to $C_{12}$ hydrocarbylaminylsilyl group, $OBR^Z_2$, or $OSO_2R^Z$, wherein $R^Z$ is a $C_1$ to $C_{12}$ hydrocarbyl group. In another aspect, each X independently can be H, $BH_4$, a halide, a $C_1$ to $C_{10}$ hydrocarbyl group, a $C_1$ to $C_{10}$ hydrocarboxy group, a $C_1$ to $C_{10}$ hydrocarbylaminyl group, a $C_1$ to $C_{10}$ hydrocarbylsilyl group, a $C_1$ to $C_{10}$ hydrocarbylaminylsilyl group, $OBR^Z_2$, or $OSO_2R^Z$, wherein $R^Z$ is a $C_1$ to $C_{10}$ hydrocarbyl group. In yet another aspect, each X independently can be H, $BH_4$, a halide, a $C_1$ to $C_8$ hydrocarbyl group, a $C_1$ to $C_8$ hydrocarboxy group, a $C_1$ to $C_8$ hydrocarbylaminyl group, a $C_1$ to $C_8$ hydrocarbylsilyl group, a $C_1$ to $C_8$ hydrocarbylaminylsilyl group, $OBR^Z_2$, or $OSO_2R^Z$, wherein $R^Z$ is a $C_1$ to $C_8$ hydrocarbyl group. In still another aspect, each X independently can be a halide or a $C_1$ to $C_{18}$ hydrocarbyl group. For example, each X can be Cl.

The hydrocarbyl group which can be an X in formula (I) can be a $C_1$ to $C_{36}$ hydrocarbyl group, including, but not limited to, a $C_1$ to $C_{36}$ alkyl group, a $C_2$ to $C_{36}$ alkenyl group, a $C_4$ to $C_{36}$ cycloalkyl group, a $C_6$ to $C_{36}$ aryl group, or a $C_7$ to $C_{36}$ aralkyl group. For instance, each X independently can be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, each X independently can be a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; alternatively, each X independently can be a $C_1$ to $C_{10}$ alkyl group, a $C_2$ to $C_{10}$ alkenyl group, a $C_4$ to $C_{10}$ cycloalkyl group, a $C_6$ to $C_{10}$ aryl group, or a $C_7$ to $C_{10}$ aralkyl group; or alternatively, each X independently can be a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be an X in formula (I) can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be an X in formula (I) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

Suitable alkenyl groups which can be an X in formula (I) can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. In one aspect, each X in formula (I) independently can be an ethenyl group, a propenyl group, a butenyl group, a pentenyl group, a hexenyl group, a heptenyl group, an octenyl group, a nonenyl group, or a decenyl group, while in another aspect, each X in formula (I) independently can be an ethenyl group, a propenyl group, a butenyl group, a pentenyl group, or a hexenyl group. For example, an X can be an ethenyl group; alternatively, a propenyl group; alternatively, a butenyl group; alternatively, a pentenyl group; or alternatively, a hexenyl group. In yet another aspect, an X can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group. Illustrative terminal alkenyl groups can include, but are not limited to, a prop-2-en-1-yl group, a bute-3-en-1-yl group, a pent-4-en-1-yl group, a hex-5-en-1-yl group, a hept-6-en-1-yl group, an octe-7-en-1-yl group, a non-8-en-1-yl group, a dece-9-en-1-yl group, and so forth.

Each X in formula (I) can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, an X in formula (I) can be a cyclopentyl group, a substituted cyclopentyl group, a cyclohexyl group, or a substituted cyclohexyl group. Moreover, each X in formula (I) independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be an X in formula (I).

In some aspects, the aryl group which can be an X in formula (I) can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be an X in formula (I).

In an aspect, the substituted phenyl group which can be an X in formula (I) can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be an X group(s) in formula (I).

In some aspects, the aralkyl group which can be an X group in formula (I) can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be an X group(s) in formula (I).

In an aspect, each non-hydrogen substituent(s) for the substituted cycloalkyl group, substituted aryl group, or substituted aralkyl group which can be an X in formula (I) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be an X in formula (I). For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group, and the like. Furthermore, the hydrocarbyl substituent can be a benzyl group, a phenyl group, a tolyl group, or a xylyl group, and the like.

A hydrocarboxy group is used generically herein to include, for instance, alkoxy, aryloxy, aralkoxy, -(alkyl, aryl, or aralkyl)-O-(alkyl, aryl, or aralkyl) groups, and —O(CO)-(hydrogen or hydrocarbyl) groups, and these groups can comprise up to 36 carbon atoms (e.g., $C_1$ to $C_{36}$, $C_1$ to $C_{18}$, $C_1$ to $C_{10}$, or $C_1$ to $C_8$ hydrocarboxy groups). Illustrative and non-limiting examples of hydrocarboxy groups which can be an X in formula (I) can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, and the like. In an aspect, the hydrocarboxy group which can be an X in formula (I) can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; or alternatively, a benzoate group.

The term hydrocarbylaminyl group is used generically herein to refer collectively to, for instance, alkylaminyl, arylaminyl, aralkylaminyl, dialkylaminyl, diarylaminyl, diaralkylaminyl, and -(alkyl, aryl, or aralkyl)-N-(alkyl, aryl, or aralkyl) groups, and unless otherwise specified, the hydrocarbylaminyl groups which can be an X in formula (I) can comprise up to 36 carbon atoms (e.g., $C_1$ to $C_{36}$, $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group which can be an X in formula (I) can be, for instance, a methylaminyl group (—NHCH$_3$), an ethylaminyl group (—NHCH$_2$CH$_3$), an n-propylaminyl group (—NHCH$_2$CH$_2$CH$_3$), an iso-propylaminyl group (—NHCH(CH$_3$)$_2$), an n-butylaminyl group (—NHCH$_2$CH$_2$CH$_2$CH$_3$), a t-butylaminyl group (—NHC(CH$_3$)$_3$), an n-pentylaminyl group (—NHCH$_2$CH$_2$CH$_2$CH$_2$CH$_3$), a neo-pentylaminyl group (—NHCH$_2$C(CH$_3$)$_3$), a phenylaminyl group (—NHC$_6$H$_5$), a tolylaminyl group (—NHC$_6$H$_4$CH$_3$), or a xylylaminyl group (—NHC$_6$H$_3$(CH$_3$)$_2$); alternatively, a methylaminyl group; alternatively, an ethylaminyl group; alternatively, a propylaminyl group; or alternatively, a phenylaminyl group. In other aspects, the hydrocarbylaminyl group which can be an X in formula (I) can be, for instance, a dimethylaminyl group (—N(CH$_3$)$_2$), a diethylaminyl group (—N(CH$_2$CH$_3$)$_2$), a di-n-propylaminyl group (—N(CH$_2$CH$_2$CH$_3$)$_2$), a di-iso-propylaminyl group (—N(CH(CH$_3$)$_2$)$_2$), a di-n-butylaminyl group (—N(CH$_2$CH$_2$CH$_2$CH$_3$)$_2$), a di-t-butylaminyl group (—N(C(CH$_3$)$_3$)$_2$), a di-n-pentylaminyl group (—N(CH$_2$CH$_2$CH$_2$CH$_2$CH$_3$)$_2$), a di-neo-pentylaminyl group (—N(CH$_2$C(CH$_3$)$_3$)$_2$), a di-phenylaminyl group (—N(C$_6$H$_5$)$_2$), a di-tolylaminyl group (—N(C$_6$H$_4$CH$_3$)$_2$), or a di-xylylaminyl group (—N(C$_6$H$_3$(CH$_3$)$_2$)$_2$); alternatively, a dimethylaminyl group; alternatively, a diethylaminyl group; alternatively, a di-n-propylaminyl group; or alternatively, a di-phenylaminyl group.

In accordance with some aspects disclosed herein, each X independently can be a $C_1$ to $C_{36}$ hydrocarbylsilyl group; alternatively, a $C_1$ to $C_{24}$ hydrocarbylsilyl group; alternatively, a $C_1$ to $C_{18}$ hydrocarbylsilyl group; or alternatively, a $C_1$ to $C_8$ hydrocarbylsilyl group. In an aspect, each hydrocarbyl (one or more) of the hydrocarbylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). As used herein, hydrocarbylsilyl is intended to cover (mono) hydrocarbylsilyl (—SiH$_2$R), dihydrocarbylsilyl (—SiHR$_2$), and trihydrocarbylsilyl (—SiR$_3$) groups, with R being a hydrocarbyl group. In one aspect, the hydrocarbylsilyl group can be a $C_3$ to $C_{36}$ or a $C_3$ to $C_{18}$ trihydrocarbylsilyl group, such as, for example, a trialkylsilyl group or a triphenylsilyl group. Illustrative and non-limiting examples of hydrocarbylsilyl groups which can be an X group(s) in formula (I) can include, but are not limited to, trimethylsilyl, triethylsilyl, tripropylsilyl (e.g., triisopropylsilyl), tributylsilyl, tripentylsilyl, triphenylsilyl, allyldimethylsilyl, and the like.

A hydrocarbylaminylsilyl group is used herein to refer to groups containing at least one hydrocarbon moiety, at least one N atom, and at least one Si atom. Illustrative and non-limiting examples of hydrocarbylaminylsilyl groups which can be an X can include, but are not limited to —N(SiMe$_3$)$_2$, —N(SiEt$_3$)$_2$, and the like. Unless otherwise specified, the hydrocarbylaminylsilyl groups which can be X can comprise up to 36 carbon atoms (e.g., C$_1$ to C$_{36}$, C$_1$ to C$_{18}$, C$_1$ to C$_{12}$, or C$_1$ to C$_8$ hydrocarbylaminylsilyl groups). In an aspect, each hydrocarbyl (one or more) of the hydrocarbylaminylsilyl group can be any hydrocarbyl group disclosed herein (e.g., a C$_1$ to C$_5$ alkyl group, a C$_2$ to C$_5$ alkenyl group, a C$_5$ to C$_8$ cycloalkyl group, a C$_6$ to C$_8$ aryl group, a C$_7$ to C$_8$ aralkyl group, etc.). Moreover, hydrocarbylaminylsilyl is intended to cover —NH(SiH$_2$R), —NH(SiHR$_2$), —NH(SiR$_3$), —N(SiH$_2$R)$_2$, —N(SiHR$_2$)$_2$, and —N(SiR$_3$)$_2$ groups, among others, with R being a hydrocarbyl group.

In an aspect, each X independently can be —OBR$^Z_2$ or —OSO$_2$R$^Z$, wherein R$^Z$ is a C$_1$ to C$_{36}$ hydrocarbyl group, or alternatively, a C$_1$ to C$_{18}$ hydrocarbyl group. The hydrocarbyl group in OBR$^Z_2$ and/or OSO$_2$R$^Z$ independently can be any hydrocarbyl group disclosed herein, such as, for instance, a C$_1$ to C$_{18}$ alkyl group, a C$_2$ to C$_{18}$ alkenyl group, a C$_4$ to C$_{18}$ cycloalkyl group, a C$_6$ to C$_{18}$ aryl group, or a C$_7$ to C$_{18}$ aralkyl group; alternatively, a C$_1$ to C$_{12}$ alkyl group, a C$_2$ to C$_{12}$ alkenyl group, a C$_4$ to C$_{12}$ cycloalkyl group, a C$_6$ to C$_{12}$ aryl group, or a C$_7$ to C$_{12}$ aralkyl group; or alternatively, a C$_1$ to C$_8$ alkyl group, a C$_2$ to C$_8$ alkenyl group, a C$_5$ to C$_8$ cycloalkyl group, a C$_6$ to C$_8$ aryl group, or a C$_7$ to C$_8$ aralkyl group.

In one aspect, each X independently can be H, BH$_4$, a halide, or a C$_1$ to C$_{36}$ hydrocarbyl group, hydrocarboxy group, hydrocarbylaminyl group, hydrocarbylsilyl group, or hydrocarbylaminylsilyl group, while in another aspect, each X independently can be H, BH$_4$, or a C$_1$ to C$_{18}$ hydrocarboxy group, hydrocarbylaminyl group, hydrocarbylsilyl group, or hydrocarbylaminylsilyl group. In yet another aspect, each X independently can be a halide; alternatively, a C$_1$ to C$_{18}$ hydrocarbyl group; alternatively, a C$_1$ to C$_{18}$ hydrocarboxy group; alternatively, a C$_1$ to C$_{18}$ hydrocarbylaminyl group; alternatively, a C$_1$ to C$_{18}$ hydrocarbylsilyl group; or alternatively, a C$_1$ to C$_{18}$ hydrocarbylaminylsilyl group. In still another aspect, each X can be H; alternatively, F; alternatively, Cl; alternatively, Br; alternatively, I; alternatively, BH$_4$; alternatively, a C$_1$ to C$_{18}$ hydrocarbyl group; alternatively, a C$_1$ to C$_{18}$ hydrocarboxy group; alternatively, a C$_1$ to C$_{18}$ hydrocarbylaminyl group; alternatively, a C$_1$ to C$_{18}$ hydrocarbylsilyl group; or alternatively, a C$_1$ to C$_{18}$ hydrocarbylaminylsilyl group.

Each X independently can be, in some aspects, H, a halide, methyl, phenyl, benzyl, an alkoxy, an aryloxy, acetylacetonate, formate, acetate, stearate, oleate, benzoate, an alkylaminyl, a dialkylaminyl, a trihydrocarbylsilyl, or a hydrocarbylaminylsilyl; alternatively, H, a halide, methyl, phenyl, or benzyl; alternatively, an alkoxy, an aryloxy, or acetylacetonate; alternatively, an alkylaminyl or a dialkylaminyl; alternatively, a trihydrocarbylsilyl or hydrocarbylaminylsilyl; alternatively, H or a halide; alternatively, methyl, phenyl, benzyl, an alkoxy, an aryloxy, acetylacetonate, an alkylaminyl, or a dialkylaminyl; alternatively, H; alternatively, a halide; alternatively, methyl; alternatively, phenyl; alternatively, benzyl; alternatively, an alkoxy; alternatively, an aryloxy; alternatively, acetylacetonate; alternatively, an alkylaminyl; alternatively, a dialkylaminyl; alternatively, a trihydrocarbylsilyl; or alternatively, a hydrocarbylaminylsilyl. In these and other aspects, the alkoxy, aryloxy, alkylaminyl, dialkylaminyl, trihydrocarbylsilyl, and hydrocarbylaminylsilyl can be a C$_1$ to C$_{36}$, a C$_1$ to C$_{18}$, a C$_1$ to C$_{12}$, or a C$_1$ to C$_8$ alkoxy, aryloxy, alkylaminyl, dialkylaminyl, trihydrocarbylsilyl, and hydrocarbylaminylsilyl.

Moreover, each X independently can be, in certain aspects, a halide or a C$_1$ to C$_{18}$ hydrocarbyl or hydrocarbylaminyl group; alternatively, a halide or a C$_1$ to C$_{18}$ hydrocarbyl group; alternatively, a halide or a C$_1$ to C$_8$ hydrocarbyl group; alternatively, F, Cl, Br, I, methyl, benzyl, or phenyl; alternatively, Cl, methyl, benzyl, or phenyl; alternatively, a C$_1$ to C$_{18}$ alkoxy, aryloxy, alkylaminyl, dialkylaminyl, trihydrocarbylsilyl, or hydrocarbylaminylsilyl group; alternatively, a C$_1$ to C$_8$ alkoxy, aryloxy, alkylaminyl, dialkylaminyl, trihydrocarbylsilyl, or hydrocarbylaminylsilyl group; or alternatively, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

In formula (I), Cp$^A$ and Cp$^B$ independently can be a substituted or unsubstituted cyclopentadienyl or indenyl group. For instance, Cp$^A$ and Cp$^B$ independently can be an unsubstituted cyclopentadienyl or indenyl group. Alternatively, Cp$^A$ and Cp$^B$ independently can be a substituted indenyl or cyclopentadienyl group, having up to 5 substituents. In one aspect, Cp$^A$ and Cp$^B$ can be cyclopentadienyl groups, and in another aspect, Cp$^A$ and Cp$^B$ can be indenyl groups, and in yet another aspect, Cp$^A$ can be a cyclopentadienyl group, and Cp$^B$ can be an indenyl group.

If present, each substituent on Cp$^A$ and Cp$^B$ independently can be H, a halide, a C$_1$ to C$_{36}$ hydrocarbyl group, a C$_1$ to C$_{36}$ halogenated hydrocarbyl group, a C$_1$ to C$_{36}$ hydrocarboxy group, or a C$_1$ to C$_{36}$ hydrocarbylsilyl group. Importantly, each substituent on Cp$^A$ and/or Cp$^B$ can be either the same or a different substituent group. Moreover, each substituent can be at any position on the respective cyclopentadienyl or indenyl ring structure that conforms with the rules of chemical valence. In an aspect, the number of substituents on Cp$^A$ and/or on Cp$^B$ and/or the positions of each substituent on Cp$^A$ and/or on Cp$^B$ are independent of each other. For instance, two or more substituents on Cp$^A$ can be different, or alternatively, each substituent on Cp$^A$ can be the same. Additionally or alternatively, two or more substituents on Cp$^B$ can be different, or alternatively, all substituents on Cp$^B$ can be the same. In another aspect, one or more of the substituents on Cp$^A$ can be different from the one or more of the substituents on Cp$^B$, or alternatively, all substituents on both Cp$^A$ and/or on Cp$^B$ can be the same. In these and other aspects, each substituent can be at any position on the respective cyclopentadienyl or indenyl ring structure. If substituted, Cp$^A$ and/or Cp$^B$ independently can have one substituent, two substituents, three substituents, or four substituents, and so forth.

In formula (I), each substituent on Cp$^A$ and/or on Cp$^B$ independently can be H, a halide, a C$_1$ to C$_{36}$ hydrocarbyl group, a C$_1$ to C$_{36}$ halogenated hydrocarbyl group, a C$_1$ to C$_{36}$ hydrocarboxy group, or a C$_1$ to C$_{36}$ hydrocarbylsilyl group. In some aspects, each substituent independently can be H; alternatively, a halide; alternatively, a C$_1$ to C$_{18}$ hydrocarbyl group; alternatively, a C$_1$ to C$_{18}$ halogenated hydrocarbyl group; alternatively, a C$_1$ to C$_{18}$ hydrocarboxy group; alternatively, a C$_1$ to C$_{18}$ hydrocarbylsilyl group; alternatively, a C$_1$ to C$_{12}$ hydrocarbyl group or a C$_1$ to C$_{12}$ hydrocarbylsilyl group; or alternatively, a C$_1$ to C$_8$ alkyl group or a C$_3$ to C$_8$ alkenyl group (e.g., a terminal alkenyl group). The halide, C$_1$ to C$_{36}$ hydrocarbyl group, C$_1$ to C$_{36}$ hydrocarboxy group, and C$_1$ to C$_{36}$ hydrocarbylsilyl group which can be a substituent on Cp$^A$ and/or on Cp$^B$ in formula (I) can be any halide, C$_1$ to C$_{36}$ hydrocarbyl group, C$_1$ to C$_{36}$ hydrocarboxy group, and C$_1$ to C$_{36}$ hydrocarbylsilyl group described herein (e.g., as pertaining to X in formula (I)). A substituent on Cp$^A$ and/or on Cp$^B$ in formula (I) can be, in certain aspects, a C$_1$ to C$_{36}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl (CF$_3$), and the like.

As a non-limiting example, if present, each substituent on Cp$^A$ and/or Cp$^B$ independently can be H, Cl, CF$_3$, a methyl group, an ethyl group, a propyl group, a butyl group (e.g., t-Bu), a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a tolyl group (or other substituted aryl group), a benzyl group, a naphthyl group, a trimethylsilyl group, a triisopropylsilyl group, a triphenylsilyl group, or an allyldimethylsilyl group; alternatively, H; alternatively, Cl; alternatively, CF$_3$; alternatively, a methyl group; alternatively, an ethyl group; alternatively, a propyl group; alternatively, a butyl group; alternatively, a pentyl group; alternatively, a hexyl group; alternatively, a heptyl group; alternatively, an octyl group, a nonyl group; alternatively, a decyl group; alternatively, an ethenyl group; alternatively, a propenyl group; alternatively, a butenyl group; alternatively, a pentenyl group; alternatively, a hexenyl group; alternatively, a heptenyl group; alternatively, an octenyl group; alternatively, a nonenyl group; alternatively, a decenyl group; alternatively, a phenyl group; alternatively, a tolyl group; alternatively, a benzyl group; alternatively, a naphthyl group; alternatively, a trimethylsilyl group; alternatively, a triisopropylsilyl group; alternatively, a triphenylsilyl group; or alternatively, an allyldimethylsilyl group.

In some aspects, Cp$^A$ and/or Cp$^B$ independently can have one substituent, and that one substituent can be a C$_1$ to C$_{18}$ hydrocarbyl group, while in other aspects, Cp$^A$ and/or Cp$^B$ independently can have one substituent, and that one substituent can be a C$_1$ to C$_8$ alkyl group or a C$_3$ to C$_8$ terminal alkenyl group.

Illustrative and non-limiting examples of unbridged metallocene compounds having formula (I) and/or suitable for use as catalyst component I can include the following three representative unbridged metallocene formulas:

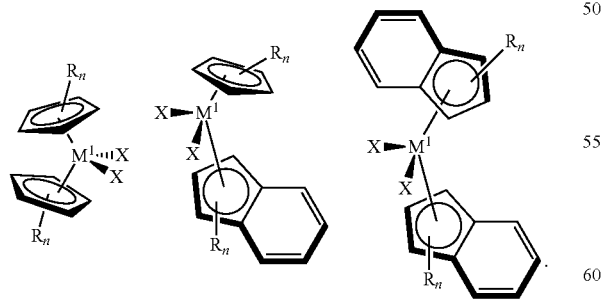

In these formulas, M$^1$ can be Zr or Hf (e.g., Zr), each X independently can be any monoanionic ligand disclosed herein (e.g., a halide), each R independently can be any substituent disclosed herein (e.g., a C$_1$ to C$_8$ alkyl group or a C$_3$ to C$_8$ terminal alkenyl group), and each n independently can be any integer that conforms to the rules of chemical valence (e.g., n can be equal to 0 (unsubstituted) or n can be equal to 1 (mono-substituted)).

Illustrative and non-limiting examples of specific unbridged metallocene compounds having formula (I) and/or suitable for use as catalyst component I can include the following compounds (Ph=phenyl):

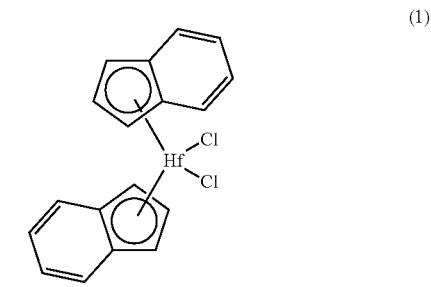
(1)

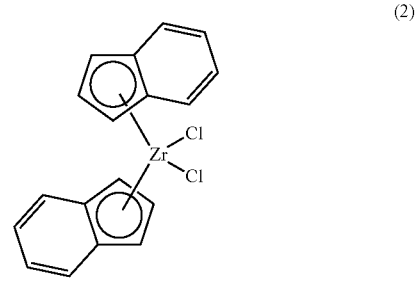
(2)

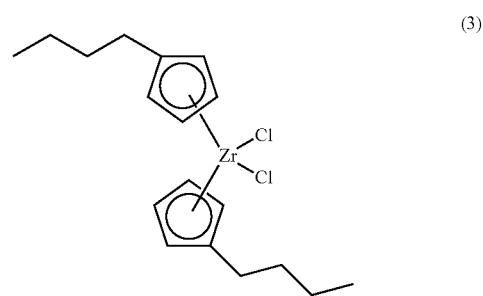
(3)

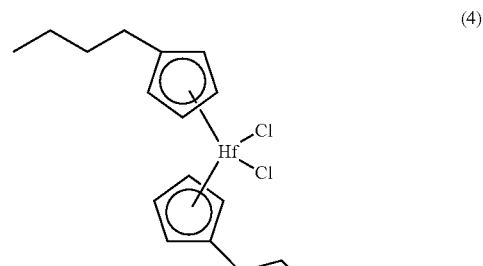
(4)

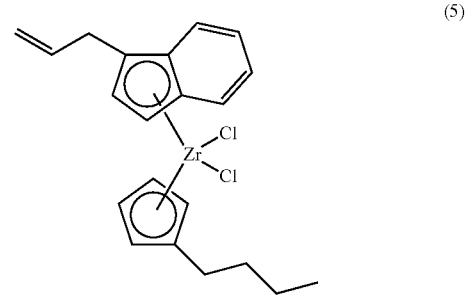
(5)

(6) 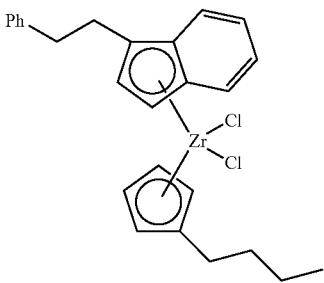

(7) 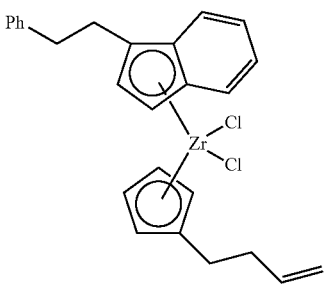

(8) 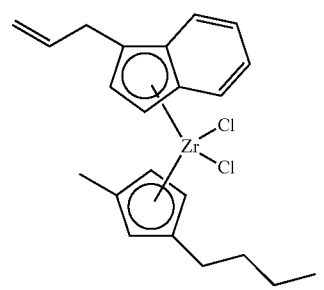

(9) 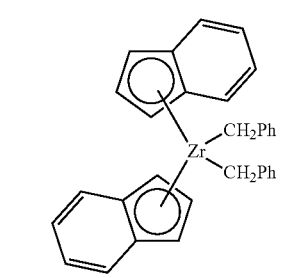

(10) 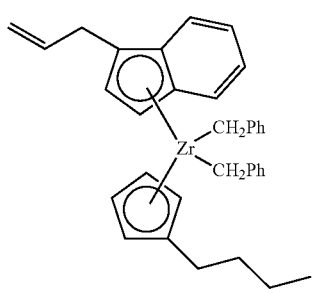

(11) 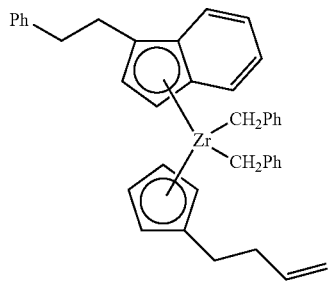

and the like, as well as combinations thereof.

Catalyst component I is not limited solely to unbridged metallocene compounds such as described above. Other suitable unbridged metallocene compounds are disclosed in U.S. Pat. Nos. 7,199,073, 7,226,886, 7,312,283, and 7,619,047, which are incorporated herein by reference in their entirety.

Catalyst Component II

Catalyst component II can comprise a bridged metallocene compound. In one aspect, for instance, catalyst component II can comprise a single atom bridged, zirconium or hafnium based metallocene compound containing two cyclopentadienyl groups. In another aspect, catalyst component II can comprise a bridged zirconium based metallocene compound containing two cyclopentadienyl groups with a carbon bridging atom or a silicon bridging atom.

In some aspects, catalyst component II can comprise a bridged zirconium (or hafnium) based metallocene compound containing two cyclopentadienyl groups, wherein the two cyclopentadienyl groups are connected by a single atom bridge, and wherein catalyst component II is capable of producing atactic polypropylene from propylene monomer. Accordingly, the appropriate isomeric form(s) of catalyst component II can be a requirement, as would be recognized by those of skill in the art.

Catalyst component II can comprise, in particular aspects of this invention, a bridged metallocene compound having formula (II):

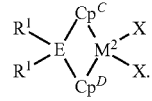 (II)

Within formula (II), $M^1$, $Cp^C$, $Cp^D$, E, each $R^1$, and each X are independent elements of the bridged metallocene compound. Accordingly, the bridged metallocene compound having formula (II) can be described using any combination of $M^2$, $Cp^C$, $Cp^D$, E, $R^1$, and X disclosed herein.

The selections for $M^2$ and each X in formula (II) are the same as those described herein for $M^1$ and X in formula (I). Therefore, $M^2$ can be Zr or Hf, and each X independently can be H, $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $-OBR^Z{}_2$, or $-OSO_2R^Z$, wherein $R^Z$ is a $C_1$ to $C_{36}$ hydrocarbyl group; alternatively, each X independently can be a halide or a $C_1$ to $C_{18}$ hydrocarbyl or hydrocarbylaminyl group; alternatively, each X independently can be a halide or a $C_1$ to $C_8$ hydrocarbyl group; or alternatively, each X can be Cl.

In formula (II), $Cp^C$ and $Cp^D$ independently can be a substituted or unsubstituted cyclopentadienyl group. For instance, $Cp^C$ and $Cp^D$ can be unsubstituted cyclopentadienyl groups (in this terminology, the bridging group is not considered to be a substitution). Alternatively, $Cp^C$ and $Cp^D$ independently can be a cyclopentadienyl group having one substituent, two substituents, or three substituents, and so forth.

If present, each substituent on $Cp^C$ and $Cp^D$ independently can be a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group. Importantly, each substituent on $Cp^C$ and/or $Cp^D$ can be either the same or a different substituent group. Moreover, each substituent can be at any position on the respective cyclopentadienyl ring structure that conforms with the rules of chemical valence. In an aspect, the number of substituents on $Cp^C$ and/or on $Cp^D$ and/or the positions of each substituent on $Cp^C$ and/or on $Cp^D$ are independent of each other. For instance, two or more substituents on $Cp^C$ can be different, or alternatively, each substituent on $Cp^C$ can be the same. Additionally or alternatively, two or more substituents on $Cp^D$ can be different, or alternatively, all substituents on $Cp^D$ can be the same. In another aspect, one or more of the substituents on $Cp^C$ can be different from the one or more of the substituents on $Cp^D$, or alternatively, all substituents on both $Cp^C$ and/or on $Cp^D$ can be the same. In these and other aspects, each substituent can be at any suitable position on the respective cyclopentadienyl ring structure. As described hereinabove, if substituted, $Cp^C$ and/or $Cp^D$ independently can have one substituent, two substituents, or three substituents, and so forth.

In formula (II), each substituent on $Cp^C$ and/or on $Cp^D$ independently can be a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group, and these substituents can be the same as those described herein for substituents on $Cp^A$ and/or on $Cp^B$ in formula (I). Accordingly, in some aspects of this invention, each substituent on $Cp^C$ and/or on $Cp^D$ independently can be a $C_1$ to $C_{18}$ hydrocarbyl group, or alternatively, a $C_1$ to $C_8$ alkyl group or a $C_3$ to $C_8$ alkenyl group (e.g., a terminal alkenyl group).

E in formula (II) can be C or Si. Thus, in one aspect, E can be C, while in another aspect, E can be Si. Each $R^1$ independently can be H or a $C_1$ to $C_{18}$ hydrocarbyl group. The $C_1$ to $C_{18}$ hydrocarbyl group which can be a $R^1$ in formula (II) can be any $C_1$ to $C_{18}$ hydrocarbyl group described herein (e.g., as pertaining to X in formula (I)). It is contemplated that each $R^1$ can be either the same or a different substituent group. For example, each $R^1$ independently can be a $C_1$ to $C_{12}$ hydrocarbyl group; alternatively, each $R^1$ independently can be a phenyl group, a $C_1$ to $C_8$ alkyl group, or a $C_3$ to $C_8$ alkenyl group; alternatively, each $R^1$ independently can be a phenyl group, a methyl group, or a $C_3$ to $C_8$ terminal alkenyl group; or alternatively, each $R^1$ independently can be a methyl group, an ethyl group, a propyl group, a butyl group, a pentyl group, a hexyl group, a heptyl group, an octyl group, a nonyl group, a decyl group, an ethenyl group, a propenyl group, a butenyl group, a pentenyl group, a hexenyl group, a heptenyl group, an octenyl group, a nonenyl group, a decenyl group, a phenyl group, a cyclohexylphenyl group, a naphthyl group, a tolyl group, or a benzyl group.

Illustrative and non-limiting examples of specific bridged metallocene compounds having formula (II) and/or suitable for use as catalyst component II can include the following compounds (Me=methyl; Ar=phenyl, substituted phenyl, or benzyl):

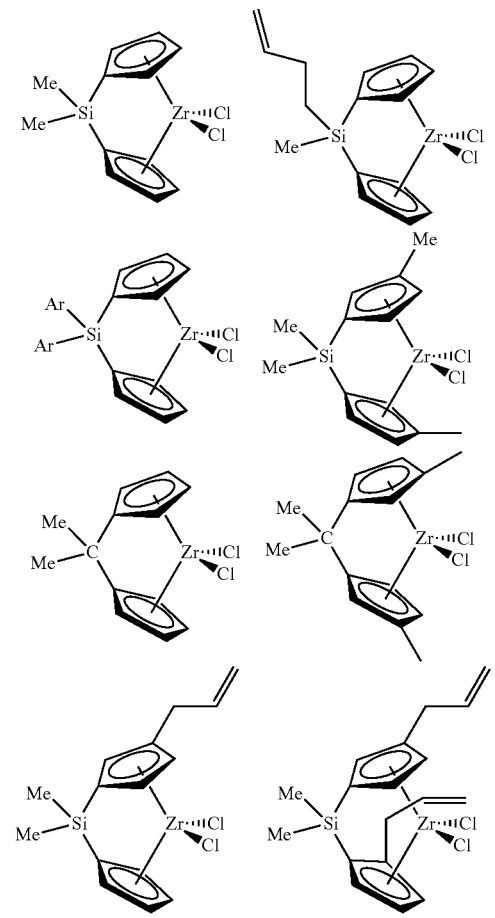

and the like, as well as combinations thereof.

Chemically-Treated Solid Oxides

In the catalyst compositions and oligomerization processes disclosed herein, any suitable chemically-treated solid oxide can be employed, whether one chemically-treated solid oxide or a mixture or combination of two or more different chemically-treated solid oxides. In one aspect, the chemically-treated solid oxide can comprise a solid oxide treated with an electron-withdrawing anion. Alternatively, in another aspect, the chemically-treated solid oxide can comprise a solid oxide treated with an electron-withdrawing anion, the solid oxide containing a Lewis-acidic metal ion. Non-limiting examples of suitable chemically-treated solid oxides are disclosed in, for instance, U.S. Pat. Nos. 7,294,599, 7,601,665, 7,884,163, 8,309,485, 8,623,973, 8,703,886, and 9,023,959, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form a chemically-treated solid oxide, either singly or in combination, can include, but are not limited to, silica-alumina, silica-titania, silica-zirconia, alumina-titania, alumina-zirconia, zinc-aluminate, alumina-boria, silica-bona, aluminophosphate-silica, and titania-zirconia. The solid oxide used herein also can encompass oxide materials such as silica-coated alumina, as described in U.S. Pat. No. 7,884,163 (e.g., Sasol Siral® 28, Sasol Siral® 40, etc.)

Accordingly, in one aspect, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another aspect, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. The solid oxides contemplated herein can have any suitable surface area, pore volume, and particle size, as would be recognized by those of skill in the art. In another aspect, the solid oxide can comprise silica, alumina, titania, zirconia, magnesia, boria, zinc oxide, any mixed oxide thereof, or any combination thereof. In yet another aspect, the solid oxide can comprise silica-alumina, silica-coated alumina, silica-titania, silica-zirconia, alumina-boria, or any combination thereof. In still another aspect, the solid oxide can comprise silica, alumina, silica-alumina, silica-coated alumina, or any mixture thereof; alternatively, silica; alternatively, alumina; alternatively, silica-alumina; or alternatively, silica-coated alumina.

The silica-coated alumina solid oxide materials which can be used in the catalyst compositions and oligomerization processes often are alumina-rich, for instance, the weight ratio of alumina to silica (alumina:silica) in the silica-coated alumina can be in a range from about 1.05:1 to about 50:1, from about 1.1:1 to about 50:1, or from about 1.2:1 to about 50:1. In one aspect, the weight ratio of alumina:silica in the silica-coated alumina can be in a range from about 1.05:1 to about 25:1; alternatively, from about 1.05:1 to about 12:1; alternatively, from about 1.05:1 to about 6:1; or alternatively, from about 1.05:1 to about 4:1. In another aspect, the weight ratio of alumina:silica in the silica-coated alumina can be in a range from about 1.1:1 to about 25:1; alternatively, from about 1.1:1 to about 12:1; alternatively, from about 1.1:1 to about 7:1; or alternatively, from about 1.1:1 to about 3:1. In yet another aspect, the weight ratio of alumina:silica in the silica-coated alumina can be in a range from about 1.2:1 to about 25:1; alternatively, from about 1.2:1 to about 12:1; alternatively, from about 1.2:1 to about 6:1; alternatively, from about 1.2:1 to about 4:1; or alternatively, from about 1.2:1 to about 3:1. In still another aspect, the weight ratio of alumina:silica in the silica-coated alumina can be in a range from about 1.3:1 to about 25:1; alternatively, from about 1.3:1 to about 12:1; alternatively, from about 1.3:1 to about 6:1; alternatively, from about 1.3:1 to about 4:1; or alternatively, from about 1.3:1 to about 3:1.

The electron-withdrawing component used to treat the solid oxide can be any component that can increase the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, acetate, fluorophosphate, trifluoroacetate, triflate, fluorozirconate, fluorotitanate, phospho-tungstate, tungstate, and molybdate, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some aspects provided herein. In other aspects, the electron-withdrawing anion can comprise sulfate, bisulfate, fluoride, chloride, bromide, iodide, fluorosulfate, fluoroborate, phosphate, acetate, fluorophosphate, trifluoroacetate, triflate, fluorozirconate, fluorotitanate, or combinations thereof. Yet, in other aspects, the electron-withdrawing anion can comprise sulfate, fluoride, chloride, or combinations thereof; alternatively, sulfate; alternatively, fluoride and chloride; or alternatively, fluoride.

The chemically-treated solid oxide generally can contain from 1 to 30 wt. % of the electron-withdrawing anion, based on the weight of the chemically-treated solid oxide. In particular aspects provided herein, the chemically-treated solid oxide can contain from about 1 to about 20 wt. %, from about 2 to about 20 wt. %, from about 3 to about 20 wt. %, from about 2 to about 15 wt. %, from about 3 to about 15 wt. %, from about 3 to about 12 wt. %, from about 4 to about 10 wt. %, or from about 5 to about 9 wt. %, of the electron-withdrawing anion, based on the total weight of the chemically-treated solid oxide.

In an aspect, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, as well as any mixture or combination thereof. In another aspect, the chemically-treated solid oxide employed in the catalyst compositions and oligomerization processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, as well as combinations thereof. In yet another aspect, the chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some aspects, the chemically-treated solid oxide can comprise a fluorided solid oxide, while in other aspects, the chemically-treated solid oxide can comprise a sulfated solid oxide.

Various processes can be used to form chemically-treated solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), various calcining procedures and conditions (e.g., calcining temperatures in a range from about 300° C.

to about 900° C., from about 400° C. to about 800° C., or from about 500° C. to about 700° C.), calcination times (e.g., calcination times in a range from about 1 minute to about 24 hours, from about 5 minutes to about 10 hours, or from about 20 minutes to about 6 hours), calcination equipment (e.g., calcination equipment such as a rotary kiln, muffle furnace, or fluidized bed, among other methods of conveying heat), and calcination atmospheres (e.g., dry or humid calcination atmospheres, oxidizing calcination atmospheres such as air or oxygen, reducing calcination atmospheres such as carbon monoxide or hydrogen, or non-reactive calcination atmospheres like nitrogen or argon) are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing chemically-treated solid oxides (e.g., chemically-treated silica-coated aluminas, such as fluorided silica-coated alumina) are well known to those of skill in the art.

Co-Catalysts

In certain aspects directed to catalyst compositions containing a co-catalyst, the co-catalyst can comprise a metal hydrocarbyl compound, examples of which can include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some aspects, the metal of the metal hydrocarbyl can be a group 1, 2, 11, 12, 13, or 14 metal; alternatively, a group 13 or 14 metal; or alternatively, a group 13 metal. Hence, in some aspects, the metal of the metal hydrocarbyl (non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some aspects, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In particular aspects directed to catalyst compositions containing a co-catalyst (e.g., the activator can comprise a solid oxide treated with an electron-withdrawing anion), the co-catalyst can comprise an aluminoxane compound, an organoboron or organoborate compound, an ionizing ionic compound, an organoaluminum compound, an organozinc compound, an organomagnesium compound, or an organolithium compound, and this can include any combinations of these materials. In one aspect, the co-catalyst can comprise an organoaluminum compound. In another aspect, the co-catalyst can comprise an aluminoxane compound, an organoboron or organoborate compound, an ionizing ionic compound, an organozinc compound, an organomagnesium compound, an organolithium compound, or any combination thereof. In yet another aspect, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof. Representative and non-limiting examples of aluminoxanes can include methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentyl-aluminoxane, neopentylaluminoxane, and the like, or any combination thereof. Representative and non-limiting examples of organoboron/organoborate compounds can include N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoro-methyl)phenyl]borate, triphenylcarbenium tetrakis[3,5-bis(trifluoromethyl)phenyl]borate, tris(pentafluorophenyl)boron, tris[3,5-bis(trifluoromethyl)phenyl]boron, and the like, or mixtures thereof.

Examples of ionizing ionic compounds can include, but are not limited to, the following compounds: tri(n-butyl) ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoro-methyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl) borate, triphenylcarbenium tetrakis[3,5-bis(trifluoromethyl)phenyl]borate, triphenylcarbenium tetrakis (pentafluorophenyl)borate, tropylium tetrakis(p-tolyl) borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis (pentafluorophenyl) borate, lithium tetrakis (pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis (pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis (pentafluorophenyl)aluminate, sodium tetraphenylaluminate, sodium tetrakis(p-tolyl)-aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, potassium tetrafluoroaluminate, and the like, or combinations thereof.

Exemplary organozinc compounds which can be used as co-catalysts can include, but are not limited to, dimethylzinc, diethylzinc, dipropylzinc, dibutylzinc, dineopentylzinc, di(trimethylsilyl)zinc, di(triethylsilyl)zinc, di(triisoproplysilyl)zinc, di(triphenylsilyl)zinc, di(allyldimethylsilyl)zinc, di(trimethylsilylmethyl)zinc, and the like, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethyl silylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, and the like, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xylyllithium, benzyllithium, (dimethylphenyl)methyllithium, allyllithium, and the like, or combinations thereof.

Co-catalysts that can be used in the catalyst compositions of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485, which are incorporated herein by reference in their entirety.

Catalyst Compositions

In some aspects, the present invention can employ catalyst compositions containing catalyst component I, catalyst component II, a chemically-treated solid oxide, and optionally, a co-catalyst.

These catalyst compositions can be utilized to oligomerize propylene to produce oligomer products, and derivatives thereof, for a variety of end-use applications. Catalyst components I are II are discussed hereinabove. In aspects of the present invention, it is contemplated that the catalyst composition can contain more than one catalyst component I metallocene compound, and/or more than one catalyst component II metallocene compound. Further, additional catalytic compounds—other than those specified as catalyst component I or II—can be employed in the catalyst compositions and/or the oligomerization processes, provided that the additional catalytic compound(s) does not detract from the advantages disclosed herein. Additionally, more than one chemically-treated solid oxide and/or more than one co-catalyst also can be utilized. Chemically-treated solid oxides and co-catalysts (e.g., organoaluminum compounds) useful in the present invention are disclosed hereinabove.

Accordingly, a catalyst composition of this invention can comprise catalyst component I, catalyst component II, a chemically-treated solid oxide, and an organoaluminum compound. For instance, the chemically-treated solid oxide can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, or combinations thereof; alternatively, the chemically-treated solid oxide can comprise (or consist essentially of, or consist of) a fluorided solid oxide and/or a sulfated solid oxide. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Therefore, a catalyst composition consistent with aspects of the invention can comprise (or consist essentially of, or consist of) an unbridged catalyst component I metallocene compound, a bridged catalyst component II metallocene compound, sulfated alumina (or fluorided silica-alumina, or fluorided silica-coated alumina, or fluorided-chlorided silica-coated alumina); and triethylaluminum (or triisobutylaluminum).

In another aspect of the present invention, a catalyst composition is provided which comprises catalyst component I, catalyst component II, a chemically-treated solid oxide, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, discussed below, in the absence of these additional materials. For example, a catalyst composition of the present invention can consist essentially of catalyst component I, catalyst component II, a chemically-treated solid oxide, and an organoaluminum compound, wherein no other materials are present in the catalyst composition which would increase/decrease the activity of the catalyst composition by more than 10% or 15% from the catalyst activity of the catalyst composition in the absence of said materials.

However, in other aspects of this invention, these co-catalysts can be employed. For example, a catalyst composition comprising catalyst component I, catalyst component II, and a chemically-treated solid oxide can further comprise an optional co-catalyst. Suitable co-catalysts in this aspect can include, but are not limited to, aluminoxane compounds, organoboron or organoborate compounds, ionizing ionic compounds, and the like, or any combination thereof; or alternatively, organoaluminum compounds, organozinc compounds, organomagnesium compounds, organolithium compounds, or any combination thereof. More than one co-catalyst can be present in the catalyst composition.

This invention further encompasses methods of making these catalyst compositions, such as, for example, contacting the respective catalyst components in any order or sequence.

According to an aspect of this invention, the weight ratio of catalyst component I to catalyst component II in the catalyst composition can be in a range from about 10:1 to about 1:10, from about 8:1 to about 1:8, from about 5:1 to about 1:5, from about 4:1 to about 1:4, from about 3:1 to about 1:3; from about 2:1 to about 1:2, from about 1.5:1 to about 1:1.5, from about 1.25:1 to about 1:1.25, or from about 1.1:1 to about 1:1.1.

Generally, the weight ratio of the co-catalyst (e.g., the organoaluminum compound) to the chemically-treated solid oxide can be in a range from about 10:1 to about 1:1000. If more than one co-catalyst compound and/or more than one chemically-treated solid oxide are employed, this ratio is based on the total weight of each respective component. In another aspect, the weight ratio of the co-catalyst (e.g., the organoaluminum compound) to the chemically-treated solid oxide can be in a range from about 3:1 to about 1:100, or from about 1:1 to about 1:50.

In some aspects of this invention, the molar ratio of the co-catalyst (e.g., the organoaluminum compound) to the metallocene compounds (total moles of catalyst component I and II) can be in a range from about 5:1 to about 5000:1; alternatively, from about 5:1 to about 1000:1; alternatively, from about 5:1 to about 250:1; or alternatively, from about 10:1 to about 150:1.

In some aspects of this invention, the weight ratio of chemically-treated solid oxide to metallocene compounds (total of catalyst component I and II) can be in a range from about 25:1 to about 5000:1. If more than one chemically-treated solid oxide is employed, this ratio is based on the total weight of the chemically-treated solid oxides. In another aspect, this weight ratio can be in a range from about 50:1 to about 1000:1, from about 50:1 to about 800:1, from about 60:1 to about 800:1, or from about 60:1 to about 600:1. Yet, in another aspect, the weight ratio of the chemically-treated solid oxide to the metallocene compounds can be in a range from about 70:1 to about 600:1 or from about 70:1 to about 500:1.

In accordance with the present invention, a process is provided that comprises contacting an olefin feedstock comprising (or consisting essentially of, or consisting of) propylene with a catalyst composition comprising (or consisting essentially of, or consisting of) catalyst component I, catalyst component II, a chemically-treated solid oxide, and an optional co-catalyst, thereby forming an oligomer product. While not being limited thereto, the molar ratio of propylene to the metallocene compounds (total moles of catalyst component I and II) often ranges from about $1 \times 10^3$:1 to about $1 \times 10^9$:1. For instance, the molar ratio of propylene to the metallocene compounds can be at least about $1 \times 10^3$:1, $5 \times 10^3$:1, $1 \times 10^4$:1, $5 \times 10^4$:1, or $1 \times 10^5$:1; alternatively or additionally, the maximum molar ratio of propylene to the metallocene compounds can be about $1 \times 10^9$:1, $5 \times 10^8$:1, $1 \times 10^8$:1, $5 \times 10^7$:1, $1 \times 10^7$:1, $5 \times 10^6$:1, or $1 \times 10^6$:1. Generally, the molar ratio of propylene to the metallocene compounds can be in a range from any minimum molar ratio disclosed herein to any maximum molar ratio disclosed herein. Therefore, suitable non-limiting ranges for the molar ratio of propylene to the metallocene compounds can include the following ranges: from about $1 \times 10^3$:1 to about $1 \times 10^9$:1, from about $5 \times 10^3$:1 to about $1 \times 10^9$:1, from about $5 \times 10^3$:1 to about $5 \times 10^8$:1, from about $1 \times 10^4$:1 to about $1 \times 10^8$:1, from about $5 \times 10^4$:1 to about $1 \times 10^8$:1, from about $5 \times 10^4$:1 to about $5 \times 10^7$:1, from about $1 \times 10^5$:1 to about $5 \times 10^7$:1, from about $1 \times 10^5$:1 to about $1 \times 10^7$:1, from about $1 \times 10^5$:1 to about $5 \times 10^6$:1, or from about $1 \times 10^5$:1 to about $1 \times 10^6$:1. Other appropriate ranges for the molar ratio of propylene to the metallocene compounds are readily apparent from this disclosure.

Unexpectedly, catalyst compositions of the present invention have a high activity. Typically, the catalyst compositions have an activity of at least about 25,000, at least about 30,000, at least about 35,000, or at least about 40,000 grams of oligomer product per gram of metallocene compounds (total of catalyst component I and catalyst component II) per hour (g/g/hr), and often can range up to about 75,000-100,000 g/g/hr. Generally, the activity of the catalyst composition can be measured at 75° C., a minimum molar ratio of propylene to the metallocene compounds of $1 \times 10^3$:1, and a reactor pressure of 500 psig. Moreover, in some aspects, the chemically-treated solid oxide can comprise sulfated alumina, fluorided silica-alumina, or fluorided silica-coated alumina, although not limited thereto.

Oligomerization Processes

Aspects of this invention are directed to propylene oligomerization processes, the production of an oligomer product, and the formation and recovery of a heavy propylene oligomer, whose typical properties are disclosed herein. A representative process can comprise (or consist essentially of, or consist of) contacting an olefin feedstock comprising propylene with a catalyst composition comprising (i) catalyst component I comprising any unbridged metallocene compound disclosed herein, (ii) catalyst component II comprising any bridged metallocene compound disclosed herein, (iii) any chemically treated solid oxide disclosed herein, and (iv) optionally, any co-catalyst disclosed herein, to form an oligomer product under oligomerization conditions.

Generally, the features of the processes (e.g., the olefin feedstock, the catalyst composition, the catalyst component I metallocene compound, the catalyst component II metallocene compound, the chemically-treated solid oxide, the co-catalyst, the materials comprising and/or features of the oligomer product, the oligomerization conditions under which the oligomer product is formed, among others) are independently described herein, and these features can be combined in any combination to further describe the disclosed processes. Moreover, additional process steps can be performed before, during, and/or after any of the steps of any of the processes disclosed herein, unless stated otherwise.

The olefin feedstock comprising propylene can come from many different sources and have a wide range of compositional attributes. In one aspect, for example, a composition comprising the olefin feedstock can comprise (a) at least about 66, 70, 74, 76, 78, 80, 82, or 84 mol % propylene, (b) less than about 34, 30, 26, 24, 22, 18, or 16 mol % $C_1$ to $C_{4+}$ paraffins, (c) less than about 4, 3, or 2 mol % $C_2$ and/or $C_{4+}$ olefins, or (d) any combination of these materials and respective amounts. In another aspect, a composition comprising the olefin feedstock can be refinery grade propylene. In another aspect, a composition comprising the olefin feedstock can comprise (a) at least about 90, 91, 92, 93, or 94 mol % propylene, (b) less than about 10, 9, 8, 7, or 6 mol % $C_1$ to $C_{4+}$ paraffins, (c) less than about 2, 1, 0.5, 0.25, or 0.1 mol % $C_2$ and/or $C_{4+}$ olefins, or (d) any combination of these materials and respective amounts. In another aspect, a composition comprising the olefin feedstock can be chemical grade propylene. In yet another aspect, a composition comprising the olefin feedstock can comprise (a) at least about 98, 98.5, 99, 99.25 or 99.5 mol % propylene, (b) less than about 2, 1.5, 1, 0.75, or 0.5 mol % $C_1$ to $C_{4+}$ paraffins, (c) less than about 0.5, 0.25, 0.1, 0.075, or 0.05 mol % $C_2$ and/or $C_{4+}$ olefins, or (d) any combination of these materials and respective amounts. In still another aspect, a composition comprising the olefin feedstock can be polymer grade propylene.

The oligomerization conditions can comprise any suitable oligomerization temperature. For example, the oligomerization temperature can be in a range from about 0° C. to about 165° C. In some aspects, the oligomerization temperature can be in a range from about 20° C. to about 160° C., from about 40° C. to about 160° C., or from about 40° C. to about 150° C., while in other aspects, the oligomerization temperature can be in a range from about 50° C. to about 150° C., from about 50° C. to about 140° C., or from about 50° C. to about 130° C. Yet, in further aspects, the oligomerization temperature can be in a range from about 60° C. to about 130° C., from about 60° C. to about 120° C., or from about 60° C. to about 90° C. Other appropriate oligomerization temperatures and temperature ranges are readily apparent from this disclosure.

The oligomerization conditions can comprise any suitable reaction pressure (or propylene partial pressure). For example, the reaction pressure (or propylene partial pressure) under which the oligomerization is conducted can be in a range from about 50 psig (344 kPa) to about 4,000 psig (27.6 MPa), from about 100 psig (689 KPa) to about 3,000 psig (20.9 MPa), or from about 150 psig (1.0 MPa) to about 2500 psig (17.2 MPa). In some aspects, the reaction pressure (or propylene partial pressure) can be in a range from about 200 psig (1.4 MPa) to about 2500 psig (17.2 MPa), from about 200 psig (1.4 MPa) to about 2,000 psig (13.8 MPa), from about 250 psig (1.4 MPa) to about 2,000 psig (1.7 MPa), or from about 250 psig (1.5 MPa) to about 1,500 psig (10.3 MPa). Other appropriate reaction pressures (or propylene partial pressures) are readily apparent from this disclosure.

In some aspects, the oligomer product can be formed in the substantial absence of hydrogen. In these aspects, no hydrogen is added to the oligomerization reaction composition. As one of ordinary skill in the art would recognize, hydrogen can be generated in-situ by metallocene catalyst compositions in various olefin oligomerization processes, and the amount generated can vary depending upon the specific catalyst composition and metallocene compound(s) employed, the type of oligomerization process used, the oligomerization reaction conditions utilized, and so forth.

In other aspects, it can be desirable to conduct the oligomerization process in the presence of a certain amount of added hydrogen, for instance, to reduce molecular weight, to reduce viscosity, etc. Accordingly, in these aspects, the oligomer product can be formed in the presence of hydrogen, i.e., the olefin feedstock (containing propylene), the catalyst composition, and hydrogen can be contacted to form the oligomer product under oligomerization conditions. For instance, the oligomer product can be formed at a hydrogen partial pressure of at least about 1 psig (6.9 kPa), 5 psig (34 kPa), 10 psig (69 kPa), 25 psig (172 kPa), or 50 psig (345 kPa); additionally or alternatively, the oligomer product can be formed at a maximum hydrogen partial pressure of about 2000 psig (13.8 MPa), 1750 psig (12.1 MPa), 1500 psig (10.3 MPa), 1250 psig (8.6 MPa), 1000 psig (6.9 MPa), 750 psig (5.2 MPa), 500 psig (3.4 MPa), or 400 psig (2.8 MPa). Generally, the hydrogen partial pressure can range from any minimum hydrogen partial pressure disclosed herein to any maximum hydrogen partial pressure disclosed herein. Therefore, suitable non-limiting ranges for the hydrogen partial pressure can include the following ranges: from about 1 psig (6.9 kPa) to about 2000 psig (13.8 MPa), from about 1 psig (6.9 kPa) to about 1750 psig (12.1 MPa), from about 5 psig (34 kPa) to about 1500 psig (10.3 MPa), from about 5 psig (34 kPa) to about 1250 psig (8.6 MPa), from about 10 psig (69 kPa) to about 1000 psig (6.9 MPa), from about 10 psig (69 kPa) to about 750 psig (5.2 MPa), from about 10 psig (69 kPa) to about 500 psig (3.5 MPa), from about 25 psig (172 kPa) to about 750 psig (5.2 MPa), from about 25 psig (172 kPa) to about 500 psig (3.4 MPa), or from about 50 psig (345 kPa) to about 500 psig (3.4 MPa). Other appropriate hydrogen partial pressures are readily apparent from this disclosure.

Any suitable reactor or vessel within an oligomerization reaction system can be used to form the oligomer product, non-limiting examples of which can include a fixed bed reactor, a stirred tank reactor, a plug flow reactor, and a loop slurry reactor, including more than one reactor in series or in parallel, and including any combination of reactor types and arrangements. In one aspect, the reaction system can comprise a single reactor (e.g., a single loop slurry rector or a single stirred tank reactor), while in another aspect, the reaction system can comprise two reactors in series (or parallel).

In the processes described herein, the catalyst composition can be deactivated. Deactivating the catalyst composition can comprise contacting the oligomer product with a suitable catalyst composition deactivating agent, or subjecting the oligomer product to suitable process steps to deactivate the catalyst composition, or a combination of both. The catalyst composition deactivating agent can comprise (or consist essentially of, or consist of) water, an alcohol compound, an amine compound, or any combination thereof; alternatively, water; alternatively, an alcohol compound; or alternatively, an amine compound. In an aspect, the alcohol compound can be a monoalcohol compound, a diol compound, a polyol compound, or any combination thereof. In some aspects, the alcohol compound can comprise, consist essentially of, or consist of, a $C_1$ to $C_{20}$ mono alcohol. In some aspects, the alcohol compound can comprise, consist essentially of, or consist of, methanol, ethanol, a propanol, a butanol, a pentanol, a hexanol, a heptanol, an octanol, a nonanol, a decanol, an undecanol, or mixtures thereof. In some aspects, the alcohol compound can comprise, consist essentially of, or consist of, methanol, ethanol, 1-propanol, 2-propanol, 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, a 1-docecanol, a 2-dodecanol, 2-ethyl-1-decanol, and mixtures thereof.

Additionally or alternatively, the catalyst composition can be deactivated by contact with an aqueous solution (e.g., an aqueous Group 1 metal hydroxide solution or an aqueous mineral acid solution). Such deactivation processes to deactivate the catalyst composition can also potentially remove a portion, or substantially all, of the metal catalyst composition components from the oligomer product.

In the processes described herein, the processes can further comprise a step of separating unreacted monomer (e.g., propylene) and the oligomer product from the catalyst composition or deactivated catalyst composition. Various suitable separations steps can be employed, as would be recognized by those of skill in the art. In an aspect, and not limited thereto, a filtration step can be used.

In some aspects, a heavy propylene oligomer can be isolated. One such technique for isolating the heavy propylene oligomer can comprise a step of removing unreacted propylene and at least a portion of the light propylene oligomers (e.g., $C_6$-$C_{12}$, etc.) from the oligomer product. In these and other aspects, various suitable separation or isolation steps can be employed, as would be recognized by those of skill in the art. In an aspect, such separation or isolation steps can include one or more batch or continuous flash processes, one or more batch or continuous distillation processes, and combinations thereof. In another aspect, a flash process at atmospheric or any suitable sub-atmospheric pressure can be utilized, while in yet another aspect, a distillation process at atmospheric or any suitable sub-atmospheric pressure can be utilized. Suitable sub-atmospheric pressures can include, but are not limited to, less than about 100 torr (13.3 kPa), less than about 50 torr (6.67 kPa), less than about 10 torr (1.33 kPa), or less than about 5 torr (0.67 kPa). The conditions that are used to isolate the heavy propylene oligomer can be varied based on the desired molecular weight properties (e.g., Mn, Mw/Mz, etc.), the desired viscosity properties (e.g., flash point, viscosity index, pour point, viscosity at 40° C., viscosity at 100° C., etc.), and the identity and/or quantity of the particular oligomer to be removed to isolate the heavy propylene oligomer. As a representative example, the separation conditions can be selected to produce a heavy propylene oligomer having a specified flash point. The flash point of the heavy propylene oligomer often can fall within a range from about 140 to about 300° C. For instance, the flash point of the heavy propylene oligomer can be at least about 140, 160, 180, 200, or 220° C.; additionally or alternatively, the maximum flash point can be about 300, 280, 260, 240, 220, or 200° C. Generally, the flash point of the heavy propylene oligomer can be in a range from any minimum flash point temperature disclosed herein to any maximum flash point temperature disclosed herein. Therefore, suitable non-limiting ranges for the flash point of the heavy propylene oligomer can include the following ranges: from about 140 to about 300° C., from about 140 to about 260° C., from about 140 to about 220° C., from about 140 to about 190° C., from about 160 to about 240° C., or from about 160 to about 200° C. Other appropriate ranges for the flash point of the heavy propylene oligomer are readily apparent from this disclosure.

In an aspect, the processes described herein can further comprise a step of hydrogenating the oligomer product (or the heavy propylene oligomer). Any suitable hydrogenation process and associated catalyst can be used, and such hydrogenation processes and catalysts (e.g., platinum, rhenium, palladium, nickel, etc.) are well known to those of skill in the art. Generally, the oligomer product or the heavy propylene oligomer can be hydrogenated to provide a hydrogenated oligomer product or hydrogenated heavy propylene oligomer having the desired degree of saturation (which can be quantified as a bromine number or bromine index). The oligomer product or the heavy propylene oligomer can be hydrogenated to provide a hydrogenated oligomer product or hydrogenated heavy propylene oligomer having any suitable bromine number or bromine index. In some aspects, the hydrogenated oligomer product or hydrogenated heavy propylene oligomer can have a maximum bromine number of about 2, 1.8, 1.6, 1.4, 1.2, or 1 gram(s) of bromine per 100 grams of sample (g Br/100 g). In other aspects, the hydrogenated oligomer product or hydrogenated heavy propylene oligomer described herein can have a maximum bromine index of about 1000, 800, 600, or 500 milligrams of bromine per 100 grams of sample (mg Br/100 g). Generally, the bromine number can be determined by ASTM D1159-09, while the bromine index can be determined by ASTM D2710-09.

The heavy propylene oligomer (or the hydrogenated heavy propylene oligomer) produced by the processes described herein can have any of the heavy propylene oligomer (or the hydrogenated heavy propylene oligomer) characteristics or properties disclosed herein (e.g., viscosity index, flash point, pour point, Mn, Mw/Mn, etc.), and in any combination. Aspects of the present invention also are directed to and encompass any heavy propylene oligomer or hydrogenated heavy propylene oligomer produced by any of the processes disclosed herein.

The flash point of the heavy propylene oligomer or the hydrogenated heavy propylene oligomer often can fall within a range from about 140 to about 300° C. For instance, the flash point of the heavy propylene oligomer or the hydrogenated heavy propylene oligomer can be at least about 140, 160, 180, 200, or 220° C.; additionally or alternatively, the maximum flash point can be about 300, 280, 260, 240, 220, or 200° C. Generally, the flash point of the heavy propylene oligomer or the hydrogenated heavy propylene oligomer can be in a range from any minimum flash point temperature disclosed herein to any maximum flash point temperature disclosed herein. Therefore, suitable non-limiting ranges for the flash point of the heavy propylene oligomer or the hydrogenated heavy propylene oligomer can include the following ranges: from about 140 to about 300° C., from about 140 to about 260° C., from about 140 to about 220° C., from about 140 to about 190° C., from about 160 to about 240° C., or from about 160 to about 200° C. Other appropriate ranges for the flash point of the heavy propylene oligomer or the hydrogenated heavy propylene oligomer are readily apparent from this disclosure. Generally, the flash point is the Cleveland open cup flash point and can be measured using ASTM D92-05.

In a particular aspect, and unexpectedly, the catalyst composition (and related oligomerization process) can produce heavy propylene oligomers or hydrogenated heavy propylene oligomers with higher flash points (and/or fire points). For instance, the flash point of the heavy propylene oligomer produced by the processes disclosed herein can be greater than that of a heavy propylene oligomer prepared using the same catalyst composition without catalyst component I, and greater than that of a heavy propylene oligomer prepared using the same catalyst composition without catalyst component II, under the same processing conditions. The same processing conditions means that all components (other than the respective metallocene components) used to prepare the catalyst compositions are held constant (e.g., same amount/type of chemically-treated solid oxide, same amount/type of co-catalyst, etc.) and all oligomerization conditions are held constant (e.g., same temperature, same pressure, same reactant ratios, etc.). Hence, the only difference is the use of the catalyst component I and catalyst component II together versus the use of, individually, catalyst component I or catalyst component II, in the oligomerization process.

In a related aspect, the flash point of the hydrogenated heavy propylene oligomer produced by the processes disclosed herein (using catalyst component I and catalyst component II) can be greater than that of a hydrogenated heavy propylene oligomer prepared using the same catalyst composition without catalyst component I, and greater than that of a hydrogenated heavy propylene oligomer prepared using the same catalyst composition without catalyst component II, under the same processing conditions.

The pour point of the heavy propylene oligomer or the hydrogenated heavy propylene oligomer typically can fall within a range from about 0 to about −60° C. For instance, the minimum pour point of the propylene oligomer can be about −60, −55, −45, −40, or −30° C.; additionally or alternatively, the maximum pour point can be about 0, −5, −8, −10, −15, or −20° C. Generally, the pour point of the heavy propylene oligomer or the hydrogenated heavy propylene oligomer can be in a range from any minimum pour point temperature disclosed herein to any maximum pour point temperature disclosed herein. Therefore, suitable non-limiting ranges for the pour point of the heavy propylene oligomer or the hydrogenated heavy propylene oligomer can include the following ranges: from about 0 to about −55° C., from about 0 to about −45° C., from about 0 to about −40° C., from about 0 to about −30° C., from about −5 to about −45° C., from about −5 to about −30° C., from about −10 to about −40° C., or from about −10 to about −30° C. Other appropriate ranges for the pour point of the heavy propylene oligomer or the hydrogenated heavy propylene oligomer are readily apparent from this disclosure. Generally, the pour point can be measured using ASTM D97-04.

The heavy propylene oligomer or the hydrogenated heavy propylene oligomer can have a viscosity index of greater than about 70. For instance, the viscosity index of the propylene oligomer or the heavy propylene oligomer can be at least about 75, 80, 85, 90, 95, or 100; additionally or alternatively, the maximum viscosity index can be about 200, 175, 150, 140, 135, 130, 125, or 120. Generally, the viscosity index of the heavy propylene oligomer or the hydrogenated heavy propylene oligomer can be in a range from any minimum viscosity index disclosed herein to any maximum viscosity index disclosed herein. Therefore, suitable non-limiting ranges for the viscosity index of the heavy propylene oligomer or the hydrogenated heavy propylene oligomer can include the following ranges: from about 75 to about 200, from about 75 to about 175, from about 80 to about 175, from about 80 to about 150, from about 80 to about 130, from about 85 to about 200, from about 85 to about 175, from about 85 to about 140, from about 90 to about 150, from about 90 to about 130, or from about 100 to about 130. Other appropriate ranges for the viscosity index of the heavy propylene oligomer or the hydrogenated heavy propylene oligomer are readily apparent from this disclosure. Generally, the viscosity index can be measured using ASTM D7042-04.

Consistent with aspects of this invention, the heavy propylene oligomer or the hydrogenated heavy propylene oligomer can have a kinematic viscosity at 40° C. ranging from about 25 to about 8000 cSt. For instance, the heavy propylene oligomer or the hydrogenated heavy propylene oligomer can have a kinematic viscosity at 40° C. of at least about 25, 50, 75, 100, 150, 175, or 200 cSt; additionally or alternatively, the maximum kinematic viscosity at 40° C. of the heavy propylene oligomer or the hydrogenated heavy propylene oligomer can be about 8000, 7000, 6000, 5000, 4000, 3000, 2000, 1500, 1000, or 800 cSt. Generally, the kinematic viscosity at 40° C. of the heavy propylene oligomer or the hydrogenated heavy propylene oligomer can be in a range from any minimum kinematic viscosity disclosed herein to any maximum kinematic viscosity disclosed herein. Therefore, suitable non-limiting ranges for the kinematic viscosity at 40° C. of the heavy propylene oligomer or the hydrogenated heavy propylene oligomer can include the following ranges: from about 25 to about 8000 cSt, from about 50 to about 6000 cSt, from about 75 to about 6000 cSt, from about 75 to about 400 cSt, from about 25 to about 800 cSt, from about 100 to about 6000 cSt, from about 100 to about 4000 cSt, from about 150 to about 6000 cSt, from about 150 to about 400 cSt, from about 150 to about 2000 cSt, from about 175 to about 2000 cSt, from about 175 to about 1500 cSt, from about 200 to about 2000 cSt, from about 200 to about 1500 cSt, or from about 200 to about 800 cSt. Other appropriate ranges for the kinematic viscosity at 40° C. of the heavy propylene oligomer or the hydrogenated heavy propylene oligomer are readily apparent from this disclosure.

The heavy propylene oligomer or the hydrogenated heavy propylene oligomer can have a kinematic viscosity at 100° C. that typically ranges from about 6 to about 200 cSt. For instance, the heavy propylene oligomer or the hydrogenated heavy propylene oligomer can have a kinematic viscosity at 100° C. of at least about 6, 8, 10, 12, or 14 cSt; additionally or alternatively, the maximum kinematic viscosity at 100° C. of the heavy propylene oligomer or the hydrogenated heavy propylene oligomer can be about 200, 175, 150, 125, 100, 80, 60, or 50 cSt. Generally, the kinematic viscosity at 100° C. of the heavy propylene oligomer or the hydrogenated heavy propylene oligomer can be in a range from any minimum kinematic viscosity disclosed herein to any maximum kinematic viscosity disclosed herein. Therefore, suitable non-limiting ranges for the kinematic viscosity at 100° C. of the heavy propylene oligomer or the hydrogenated heavy propylene oligomer can include the following ranges: from about 6 to about 200 cSt, from about 8 to about 150 cSt, from about 10 to about 150 cSt, from about 10 to about 100 cSt, from about 12 to about 150 cSt, from about 12 to about 100 cSt, from about 12 to about 80 cSt, from about 12 to about 60 cSt, or from about 14 to about 50 cSt. Other appropriate ranges for the kinematic viscosity at 100° C. of the heavy propylene oligomer or the hydrogenated heavy propylene oligomer are readily apparent from this disclosure. Generally, the viscosities can be measured using ASTM D7042-04 or ASTM D445-06.

All molecular weights (Mp is the peak molecular weight, Mn is the number-average molecular weight, Mw is the weight-average molecular weight, and Mz is the z-average molecular weight) relating to the propylene oligomers disclosed herein were determined using the GPC procedure described herein using the molecular weight standards described herein. Due to limitations in the utilized GPC procedure and equipment, materials with molecular weights under approximately 125-150 g/mol may not be fully represented in the molecular weight distribution. For example, some $C_9$ compounds can be excluded from the molecular weight distribution because their boiling points were similar to that of sample preparation temperatures.

In an aspect, the heavy propylene oligomer or the hydrogenated heavy propylene oligomer can have a Mn in a range from about 250 to about 10,000 g/mol. For instance, the Mn of the heavy propylene oligomer or the hydrogenated heavy propylene oligomer can be at least about 250, 325, 400, 500, 600, 650, 700, or 750 g/mol; additionally or alternatively, the maximum Mn can be about 10,000, 7500, 6000, 5000, 4000, 3000, 2500, or 2000 g/mol. Generally, the Mn of the heavy propylene oligomer or the hydrogenated heavy propylene oligomer can be in a range from any minimum Mn disclosed herein to any maximum Mn disclosed herein. Therefore, suitable non-limiting ranges for the Mn of the heavy propylene oligomer or the hydrogenated heavy propylene oligomer can include the following ranges: from about 250 to about 5000 g/mol, from about 400 to about 7500 g/mol, from about 500 to about 5000 g/mol, from about 500 to about 4000 g/mol, from about 500 to about 2500 g/mol, from about 600 to about 2500 g/mol, or from about 750 to about 2500 g/mol. Other appropriate ranges for the Mn of the heavy propylene oligomer or the hydrogenated heavy propylene oligomer are readily apparent from this disclosure.

While not being limited thereto, the heavy propylene oligomer or the hydrogenated heavy propylene oligomer often can have a Mw in a range from about 500 to about 10,000 g/mol. For instance, the Mw of the heavy propylene oligomer or the hydrogenated heavy propylene oligomer can be at least about 500, 750, 1000, 1250, or 1500 g/mol; additionally or alternatively, the maximum Mw can be about 10,000, 9000, 7000, 5000, 4000, or 3000 g/mol. Generally, the Mw of the heavy propylene oligomer or the hydrogenated heavy propylene oligomer can be in a range from any minimum Mw disclosed herein to any maximum Mw disclosed herein. Therefore, suitable non-limiting ranges for the Mw of the heavy propylene oligomer or the hydrogenated heavy propylene oligomer can include the following ranges: from about 500 to about 10,000 g/mol, from about 750 to about 9000 g/mol, from about 750 to about 7000 g/mol, from about 1000 to about 5000 g/mol, from about 500 to about 4000 g/mol, from about 500 to about 3000 g/mol, from about 1000 to about 5000 g/mol, or from about 1500 to about 5000 g/mol. Other appropriate ranges for the Mw of the heavy propylene oligomer or the hydrogenated heavy propylene oligomer are readily apparent from this disclosure.

The ratio of Mw/Mn, often referred to as the polydispersity index, of the heavy propylene oligomer or the hydrogenated heavy propylene oligomer typically can range from about 1.6 to about 5. For instance, the Mw/Mn of the heavy propylene oligomer or the hydrogenated heavy propylene oligomer can be at least about 1.6, 1.7, 1.8, 1.9, or 2; additionally or alternatively, the maximum Mw/Mn can be about 5, 4.5, 4, or 3.5. Generally, the Mw/Mn of the heavy propylene oligomer or the hydrogenated heavy propylene oligomer can be in a range from any minimum Mw/Mn disclosed herein to any maximum Mw/Mn disclosed herein. Therefore, suitable non-limiting ranges for the Mw/Mn of the heavy propylene oligomer or the hydrogenated heavy propylene oligomer can include the following ranges: from about 1.6 to about 5, from about 1.8 to about 5, from about 1.8 to about 4.5, from about 1.9 to about 4, or from about 2 to about 4. Other appropriate ranges for the Mw/Mn of the heavy propylene oligomer or the hydrogenated heavy propylene oligomer are readily apparent from this disclosure.

The ratio of Mz/Mw of the heavy propylene oligomer or the hydrogenated heavy propylene oligomer typically can range from about 1.9 to about 8. For instance, the Mz/Mw of the heavy propylene oligomer or the hydrogenated heavy propylene oligomer can be at least about 1.9, 2, or 2.2; additionally or alternatively, the maximum Mz/Mw can be about 8, 6, 5, or 3. Generally, the Mz/Mw of the heavy propylene oligomer or the hydrogenated heavy propylene oligomer can be in a range from any minimum Mz/Mw disclosed herein to any maximum Mz/Mw disclosed herein. Therefore, suitable non-limiting ranges for the Mz/Mw of the heavy propylene oligomer or the hydrogenated heavy propylene oligomer can include the following ranges: from about 1.9 to about 8, from about 1.9 to about 6, from about 1.9 to about 5, from about 1.9 to about 3, from about 2 to about 8, from about 2 to about 6, from about 2.2 to about 8, or from about 2.2 to about 5. Other appropriate ranges for the Mz/Mw of the heavy propylene oligomer or the hydrogenated heavy propylene oligomer are readily apparent from this disclosure.

The tacticity (e.g., the atactic content) of the heavy propylene oligomer or the hydrogenated heavy propylene oligomer can be quantified by the mr triad content, and the mr triad content can fall within a range from about 40 to about 50 mol %. For instance, the mr triad content of the heavy propylene oligomer or the hydrogenated heavy propylene oligomer can be at least about 40, 41, 42, 43, 44, or 45%; additionally or alternatively, the maximum mr triad content can be about 50, 49, 48, or 47%. Generally, the mr triad content of the heavy propylene oligomer or the hydrogenated heavy propylene oligomer can be in a range from any minimum mr triad content disclosed herein to any maximum mr triad content disclosed herein. Therefore, suitable non-limiting ranges for the mr triad content of heavy propylene oligomer or the hydrogenated heavy propylene oligomer can include the following ranges: from about 40 to about 50%, from about 41 to about 49%, from about 42 to about 50%, from about 42 to about 49%, from about 43 to about 48%, from about 44 to about 49%, or from about 45 to about 50%. Other appropriate ranges for the mr triad content of the heavy propylene oligomer or the hydrogenated heavy propylene oligomer are readily apparent from this disclosure.

In aspects of this invention, the repeating units of the heavy propylene oligomer or the hydrogenated heavy propylene oligomer can be substantially all propylene units. That is, the repeating units of the heavy propylene oligomer or the hydrogenated heavy propylene oligomer can contain at least about 98 mol % propylene units, and in some aspects, at least about 98.5 mol % propylene units, at least about 99 mol % propylene units, at least about 99.25 mol % propylene units, at least about 99.5 mol % propylene units, or at least about 99.75 mol % propylene units.

The heavy propylene oligomer or the hydrogenated heavy propylene oligomer can be a liquid propylene oligomer in particular aspects of this invention. Thus, the heavy propylene oligomer or the hydrogenated heavy propylene oligomer can be a liquid (not a solid or gas) at standard temperature (25° C.) and pressure (1 atm).

An illustrative and non-limiting example of a heavy propylene oligomer or hydrogenated heavy propylene oligomer produced in accordance with the present invention can have a Mn in a range from about 600 to about 2500 g/mol, and/or a Mw in a range from about 1500 to about 5000 g/mol, and/or a ratio of Mw/Mn in a range from about 1.8 to about 4.5, and/or a ratio of Mz/Mw in a range from about 1.9 to about 5, and/or a viscosity index in a range from about 80 to about 130, and/or a pour point in a range from about −5 to about −30° C., and/or a flash point in a range from about 140 to about 260° C., and/or a kinematic viscosity at 40° C. in a range from about 200 to about 1500 cSt, and/or a kinematic viscosity at 100° C. in a range from about 14 to about 50 cSt.

This invention also contemplates and encompasses any compositions (e.g., lubricant compositions or lubricant formulations) or base oils that comprise the heavy propylene oligomers or the hydrogenated heavy propylene oligomers disclosed herein. Such lubricant compositions or formulations can include one or more suitable additions, such as viscosity index improvers/viscosity modifiers/viscosity improvers, dispersants (metallic and/or non-metallic), detergents (metallic and/or non-metallic), friction modifiers, traction improving additives, demulsifiers, defoamants, antioxidants, anti-wear additives (metallic and non-metallic, phosphorus-containing and non-phosphorus, sulfur-containing and non-sulfur types), extreme-pressure additives (metallic and non-metallic, phosphorus-containing and non-phosphorus, sulfur-containing and non-sulfur types), anti-rust additives, corrosion inhibitors, metal deactivators, anti-seizure agents, pour point depressants, wax modifiers, seal compatibility agents, friction modifiers, lubricity agents, anti-staining agents, chromophores (dyes), haze inhibitors, and the like. Additional information on additives used in lubricant formulations can be found in "Fuels and Lubricants Handbook: Technology, Properties, Performance, and Testing" edited by George E. Totten, Steven R. Westbrook, Rajesh J. Shah, ASTM (2003), ISBN 0-8031-2096-6; Chapter 9 Additives and Additive Chemistry, pp. 199-248, "Lubricants and Related Products," Klamann, Verlag Chemie, Deerfield Beach, Fla., ISBN 0-89573-177-0; "Lubricant Additives" by M. W. Ranney, published by Noyes Data Corporation of Parkridge, N.J. (1973); "Lubricants and Lubrications," T. Mang and W. Dresel, eds., Wiley-VCH GmbH, Weinheim (2001); and "Lubricant Additives", C. V. Smallheer and R. K. Smith, published by the Lezius-Hiles Co. of Cleveland, Ohio (1967).

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Kinematic viscosities at 100° C. and 40° C. were determined in accordance with ASTM D7042-04 (Stabinder viscometer method) or ASTM D445-06 (capillary tube method) at the respective temperatures, and the results are reported in centistokes (cSt). The viscosity index was determined in accordance with ASTM D2270-10e1, using the tables provided therein for viscosity data determined at 100° C. and 40° C. Pour point is a measurement of the temperature at which the sample will begin to flow under carefully controlled conditions. Pour point was determined in accordance with ASTM D97-04 or ASTM D5950-02 (2007) (automatic tilt method), and the results are reported in ° C. Flash point (Cleveland open cup) and Fire Point were determined in accordance with ASTM D92-05.

Molecular weights and molecular weight distributions were obtained using a PL-GPC 220 (Polymer Labs, an Agilent Company) composition equipped with a IR4 detector (Polymer Char, Spain) and three Styragel® HMW-6E GPC columns (Waters Corp., MA) running at 145° C. The flow rate of the mobile phase, 1,2,4-trichlorobenzene (TCB) containing 0.5 g/L 2,6-di-t-butyl-4-methylphenol (BHT), was set at 1 mL/min, and oligomer solution concentrations were in the range of 1.0-1.5 mg/mL, depending on the molecular weight. Sample preparation of the oligomer composition was conducted at 150° C. for nominally 4 hr with occasional and gentle agitation, before the solutions were transferred to sample vials for injection. An injection volume of approximately 200 μL was used. The integral calibration method was used to deduce molecular weights and molecular weight distributions using a Chevron Phillips Chemicals Company's HDPE polyethylene resin, MARLEX® BHB5003, as the standard (calibration samples of MARLEX® BHB5003 can be obtained from Chevron Phillips Chemicals Company, LP). The integral table of the standard was pre-determined in a separate experiment with SEC-MALS. Mn is the number-average molecular weight, Mw is the weight-average molecular weight, Mz is the z-average molecular weight, and Mp is the peak molecular weight.

Triad determination and the tacticity of the oligomer product and/or the heavy propylene oligomer can be determined utilizing $^1$HNMR or $^{13}$C NMR peak intensities and the methods as described in Il Kim, Jia-Min Zhou and Hoeil Chung, "Higher α-Olefin Polymerization by Zr Complex", J. of *Polymer Science: Part A: Polymer Chemistry*, Vol. 38, 1687-1697 (2000).

Fluorided silica-coated alumina (FSCA) was prepared as follows. Alumina A from W. R. Grace having a surface area of 300 m$^2$/g, a pore volume of 1.2 mL/g, and an average particle size of 100 microns, was first calcined in dry air for 6 hours at 600° C., then cooled to ambient temperature, followed by contacting with tetraethylorthosilicate in isopropanol to equal 25 wt. % SiO$_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina (FSCA) was collected and stored under dry nitrogen, and was used without exposure to the atmosphere.

In the examples that follow, MET A is bis(n-propylcyclopentadienyl) zirconium dichloride, and MET B is (n-butyl)$_2$-Si bridged bis-cyclopentadienyl zirconium dichloride.

Examples 1-3

Examples 1-3 were performed using the following equipment and procedure. The base of a 1 gallon (3.79 liter) autoclave, under a purge of nitrogen gas, was charged sequentially with the fluorided silica-coated alumina, triisobutylaluminum (1 molar solution in heptanes), and a 1 mg/mL toluene solution of the metallocene compound(s). The autoclave was then sealed and charged with 2.5 liters of liquid propylene under a pressure of 150 to 200 psig (1.03 to 1.38 MPa). Hydrogen was then allowed to flow from a 300 mL pressure vessel charged to 620 psig (4.27 MPa) with hydrogen until the desired pressure drop in the hydrogen charge vessel pressure was achieved. The autoclave was then heated to the desired temperature and the reaction proceeded, with stirring, for one hour. Generally, the reactor pressure was approximately 500 psig (3.45 MPa) for a reaction temperature of 75° C. The reactor was then cooled to 40° C. The reactor was then vented to a flare line to allow the unreacted propylene to vent from the reactor. The liquid product was collected and filtered to remove the FSCA. The filtrate was then subjected to rotary evaporation at 100° C. for one hour under a reduced pressure of 5 torr (0.67 kPa) to 10 torr (1.33 kPa). The rotary evaporated liquid was then placed under vacuum, with stirring, at 3 torr (0.40 kPa) and 135° C. for one hour to provide a viscous oil (after volatile removal).

Table I summarizes the metallocene compound(s) used, oligomerization conditions, product weights, and catalyst activities for Examples 1-3. In Table I, MET is the metallocene compound(s) used, MET (mg) is the weight of the metallocene compound(s) used, FSCA (mg) is the weight of the fluorided silica-coated alumina used, TIBA (mL) is the amount of a 1M triisobutylaluminum solution of co-catalyst used, ΔH$_2$ is the amount of hydrogen used (based on pressure drop), Temp (° C.) is the oligomerization reaction temperature used, Time (min) is the reaction time, Prod Wt. (g) is the weight of the oligomer product produced prior to rotary evaporation, and the catalyst activities shown are based on the metallocene(s) (g oligomer product per gram of metallocene compound(s) per hour–g product/g metallocene/hr), and based on the FSCA (g oligomer product per gram of FSCA per hour–g product/g FSCA/hr). As shown in Table I, and unexpectedly, catalyst activities were very high, ranging from 60,000-100,000 g product/g metallocene/hr and from 400-650 g product/g FSCA/hr.

For Examples 1-3, Table II provides the molecular weight distribution data for the liquid product prior to the filtration step to remove the FSCA, the molecular weight distribution data for the viscous oil obtained after subjecting the rotary evaporated liquid to 3 torr (0.40 kPa) and 135° C. for one hour (after volatile removal), and the physical properties (40° C. and 100° C. kinematic viscosities, viscosity index, pour point, flash point and fire points) for the viscous oil obtained after subjecting the rotary evaporated liquid to 3 torr (0.40 kPa) and 135° C. for one hour (after volatile removal). In Table II, Ex is the example number, the molecular weight properties are shown in kg/mol, VI is the viscosity index, Vis 40 is the 40° C. kinematic viscosity in cSt, Vis 100 is the 100° C. kinematic viscosity in cSt, Flash/Fire are the respective flash and fire points (° C.), and Pour Point is shown in ° C.

As shown in Table II, most of the properties of the viscous oil product of Example 3 (produced using MET A and MET B) were between those of Example 1 (MET A) and Example 2 (MET B). However, unexpectedly and beneficially, the flash point of the viscous oil product of Example 3 was significantly higher than the flash points of Example 1 and Example 2 (~30-50° C. higher). Likewise, the fire point of the viscous oil product of Example 3 was significantly higher than the fire points of Example 1 and Example 2 (~30-35° C. higher). Thus, the dual metallocene catalyst system provided a synergistic improvement in flash point (and fire point) over that achieved using either single metallocene based catalyst system.

TABLE I

| Example | MET | MET (mg) | FSCA (mg) | TIBA (mL) | Δ H₂ (psig) | Temp (° C.) | Time (min) | Prod Wt. (g) | Activities (g product/g metallocene or g FSCA/hour) | |
|---|---|---|---|---|---|---|---|---|---|---|
| | | | | | | | | | Based on metallocene | Based on FSCA |
| 1 | MET A | 2 | 300 | 0.5 | 50 | 75 | 60 | 190 | 95,000 | 633 |
| 2 | MET B | 2 | 300 | 0.5 | 50 | 75 | 60 | 121 | 60,500 | 403 |
| 3 | MET A/MET B | 1/1 | 300 | 0.5 | 50 | 75 | 60 | 123 | 61,500 | 410 |

TABLE II

| | Molecular Weight Distribution Data (molecular weights in kg/mol) | | | | | | | Properties After Volatile Component Removal | | | | |
|---|---|---|---|---|---|---|---|---|---|---|---|---|
| Ex | | Mn | Mw | Mz | Mv | Mp | Mw/Mn | Mz/Mw | VI | Vis 40 (cSt) | Vis 100 (cSt) | Flash/ Fire | Pour Point |
| 1 | Crude Product | 0.57 | 2.28 | 7.07 | 1.95 | 1.41 | 4.00 | 3.10 | 121 | 498 | 34.9 | 149/209 | −25 |
| | After Volatile Removal | 0.75 | 2.45 | 8.16 | 2.11 | 1.34 | 3.27 | 3.33 | | | | | |
| 2 | Crude Product | 1.33 | 2.83 | 5.35 | 2.61 | 2.32 | 2.13 | 1.89 | 103 | 1176 | 60.0 | 165/211 | −15 |
| | After Volatile Removal | 1.54 | 2.90 | 5.15 | 2.70 | 2.29 | 1.88 | 1.78 | | | | | |
| 3 | Crude Product | 1.00 | 2.30 | 4.97 | 2.08 | 1.75 | 2.30 | 2.16 | 115 | 470 | 35.7 | 197/243 | −22 |
| | After Volatile Removal | 1.32 | 2.57 | 5.43 | 2.36 | 1.68 | 1.95 | 2.11 | | | | | |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process comprising:
contacting an olefin feedstock comprising propylene with a catalyst composition comprising (i) catalyst component I comprising any unbridged metallocene compound disclosed herein, (ii) catalyst component II comprising any bridged metallocene compound disclosed herein, (iii) any chemically-treated solid oxide disclosed herein, and (iv) optionally, any co-catalyst disclosed herein, to form an oligomer product under oligomerization conditions.

Aspect 2. The process defined in aspect 1, wherein catalyst component I comprises an unbridged zirconium or hafnium based metallocene compound containing two cyclopentadienyl groups, two indenyl groups, or a cyclopentadienyl and an indenyl group.

Aspect 3. The process defined in aspect 1, wherein catalyst component I comprises an unbridged zirconium or hafnium based metallocene compound containing two cyclopentadienyl groups.

Aspect 4. The process defined in aspect 1, wherein catalyst component I comprises an unbridged zirconium or hafnium based metallocene compound containing two indenyl groups.

Aspect 5. The process defined in aspect 1, wherein catalyst component I comprises an unbridged zirconium or hafnium based metallocene compound containing a cyclopentadienyl and an indenyl group.

Aspect 6. The process defined in aspect 1, wherein catalyst component I comprises an unbridged metallocene compound having formula (I):

(I)

wherein $M^1$ is Zr or Hf, $Cp^A$ and $Cp^B$ independently are any cyclopentadienyl or indenyl group disclosed herein, and each X independently is any monoanionic ligand disclosed herein.

Aspect 7. The process defined in aspect 6, wherein $M^1$ is Zr.

Aspect 8. The process defined in aspect 6, wherein $M^1$ is Hf.

Aspect 9. The process defined in any one of aspects 6-8, wherein $Cp^A$ and $Cp^B$ are cyclopentadienyl groups.

Aspect 10. The process defined in any one of aspects 6-8, wherein $Cp^A$ and $Cp^B$ are indenyl groups.

Aspect 11. The process defined in any one of aspects 6-8, wherein $Cp^A$ is a cyclopentadienyl group, and $Cp^B$ is an indenyl group.

Aspect 12. The process defined in any one of aspects 6-11, wherein $Cp^A$ is substituted with any suitable substituent, any suitable number of substituents, and at any suitable position(s) that conforms to the rules of chemical valence.

Aspect 13. The process defined in any one of aspects 6-12, wherein $Cp^A$ is substituted, and each substituent independently is any substituent disclosed herein, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 14. The process defined in any one of aspects 6-13, wherein $Cp^A$ is substituted, and each substituent independently is a hydrocarbyl group having up to 18 carbon atoms.

Aspect 15. The process defined in any one of aspects 6-14, wherein $Cp^A$ is substituted, and each substituent independently is an alkyl group (e.g., a $C_1$ to $C_8$ alkyl group) or an alkenyl group (e.g., a $C_3$ to $C_8$ terminal alkenyl group).

Aspect 16. The process defined in any one of aspects 6-11, wherein $Cp^A$ is unsubstituted.

Aspect 17. The process defined in any one of aspects 6-16, wherein $Cp^B$ is substituted with any suitable substituent, any suitable number of substituents, and at any suitable position(s) that conforms to the rules of chemical valence.

Aspect 18. The process defined in any one of aspects 6-17, wherein $Cp^B$ is substituted, and each substituent independently is any substituent disclosed herein, e.g., H, a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 19. The process defined in any one of aspects 6-18, wherein $Cp^B$ is substituted, and each substituent independently is a hydrocarbyl group having up to 18 carbon atoms.

Aspect 20. The process defined in any one of aspects 6-19, wherein $Cp^B$ is substituted, and each substituent independently is an alkyl group (e.g., a $C_1$ to $C_8$ alkyl group) or an alkenyl group (e.g., a $C_3$ to $C_8$ terminal alkenyl group).

Aspect 21. The process defined in any one of aspects 6-16, wherein $Cp^B$ is unsubstituted.

Aspect 22. The process defined in any one of aspects 1-21, wherein catalyst component II comprises a single atom bridged, zirconium or hafnium based metallocene compound containing two cyclopentadienyl groups.

Aspect 23. The process defined in any one of aspects 1-21, wherein catalyst component II comprises a bridged zirconium based metallocene compound containing two cyclopentadienyl groups with a carbon bridging atom or a silicon bridging atom.

Aspect 24. The process defined in any one of aspects 1-21, wherein catalyst component II comprises a bridged metallocene compound having formula (II):

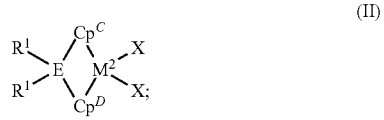

(II)

wherein $M^2$ is Zr or Hf, $Cp^C$ and $Cp^D$ independently are any cyclopentadienyl groups disclosed herein, E is C or Si, each $R^1$ independently is H or any $C_1$ to $C_{18}$ hydrocarbyl group disclosed herein, and each X independently is any monoanionic ligand disclosed herein.

Aspect 25. The process defined in aspect 24, wherein $M^2$ is Zr.

Aspect 26. The process defined in aspect 24, wherein $M^2$ is Hf.

Aspect 27. The process defined in any one of aspects 24-26, wherein $Cp^C$ is substituted with any suitable substituent, any suitable number of substituents, and at any suitable position(s) that conforms to the rules of chemical valence.

Aspect 28. The process defined in any one of aspects 24-27, wherein $Cp^C$ is substituted, and each substituent independently is any substituent disclosed herein, e.g., a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 29. The process defined in any one of aspects 24-28, wherein $Cp^C$ is substituted, and each substituent independently is a hydrocarbyl group having up to 18 carbon atoms.

Aspect 30. The process defined in any one of aspects 24-29, wherein $Cp^C$ is substituted, and each substituent independently is an alkyl group (e.g., a $C_1$ to $C_8$ alkyl group) or an alkenyl group (e.g., a $C_3$ to $C_8$ terminal alkenyl group).

Aspect 31. The process defined in any one of aspects 24-26, wherein $Cp^C$ is unsubstituted.

Aspect 32. The process defined in any one of aspects 24-31, wherein $Cp^D$ is substituted with any suitable substituent, any suitable number of substituents, and at any suitable position(s) that conforms to the rules of chemical valence.

Aspect 33. The process defined in any one of aspects 24-32, wherein $Cp^D$ is substituted, and each substituent independently is any substituent disclosed herein, e.g., a halide, a $C_1$ to $C_{36}$ hydrocarbyl group, a $C_1$ to $C_{36}$ halogenated hydrocarbyl group, a $C_1$ to $C_{36}$ hydrocarboxy group, or a $C_1$ to $C_{36}$ hydrocarbylsilyl group.

Aspect 34. The process defined in any one of aspects 24-33, wherein $Cp^D$ is substituted, and each substituent independently is a hydrocarbyl group having up to 18 carbon atoms.

Aspect 35. The process defined in any one of aspects 24-34, wherein $Cp^D$ is substituted, and each substituent independently is an alkyl group (e.g., a $C_1$ to $C_8$ alkyl group) or an alkenyl group (e.g., a $C_3$ to $C_8$ terminal alkenyl group).

Aspect 36. The process defined in any one of aspects 24-31, wherein $Cp^D$ is unsubstituted.

Aspect 37. The process defined in any one of aspects 24-36, wherein E is C.

Aspect 38. The process defined in any one of aspects 24-36, wherein E is Si.

Aspect 39. The process defined in any one of aspects 24-38, wherein each $R^1$ independently is a $C_1$ to $C_{12}$ hydrocarbyl group.

Aspect 40. The process defined in any one of aspects 24-39, wherein each $R^1$ independently is a phenyl group, a $C_1$ to $C_8$ alkyl group, or a $C_3$ to $C_8$ alkenyl group.

Aspect 41. The process defined in any one of aspects 24-40, wherein each $R^1$ independently is a phenyl group, a methyl group, or a $C_3$ to $C_8$ terminal alkenyl group.

Aspect 42. The process defined in any one of aspects 6-21 or 24-41, wherein each X independently is H, $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, $OBR^Z_2$, or $OSO_2R^Z$, wherein $R^Z$ is a $C_1$ to $C_{36}$ hydrocarbyl group.

Aspect 43. The process defined in any one of aspects 6-21 or 24-41, wherein each X independently is any halide or $C_1$ to $C_{18}$ hydrocarbyl or hydrocarbylaminyl group disclosed herein.

Aspect 44. The process defined in any one of aspects 6-21 or 24-41, wherein each X independently is any halide disclosed herein.

Aspect 45. The process defined in any one of aspects 6-21 or 24-41, wherein each X is Cl.

Aspect 46. The process defined in any one of the preceding aspects, wherein a weight ratio of catalyst component I to catalyst component II in the catalyst composition is in any range disclosed herein, e.g., from about 10:1 to about 1:10, from about 5:1 to about 1:5, from about 2:1 to about 1:2, etc.

Aspect 47. The process defined in any one of the preceding aspects, wherein the chemically-treated solid oxide comprises a solid oxide treated with an electron-withdrawing anion, e.g., any solid oxide and any electron-withdrawing anion disclosed herein.

Aspect 48. The process defined in aspect 47, wherein (a) the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof, and (b) the electron-withdrawing anion comprises sulfate, bisulfate, fluoride, chloride, bromide, iodide, fluorosulfate, fluoroborate, phosphate, acetate, fluorophosphate, trifluoroacetate, triflate, fluorozirconate, fluorotitanate, phospho-tungstate, or any combination thereof.

Aspect 49. The process defined in aspect 47 or 48, wherein the solid oxide comprises silica, alumina, silica-alumina, silica-coated alumina, or a mixture thereof.

Aspect 50. The process defined in aspect 47 or 48, wherein the solid oxide comprises silica-coated alumina.

Aspect 51. The process defined in any one of aspects 47-50, wherein the electron-withdrawing anion comprises sulfate, fluoride, chloride, or any combination thereof.

Aspect 52. The process defined in any one of aspects 47-50, wherein the electron-withdrawing anion comprises sulfate.

Aspect 53. The process defined in any one of aspects 47-50, wherein the electron-withdrawing anion comprises fluoride, chloride, or both.

Aspect 54. The process defined in any one of aspects 1-46, wherein the chemically-treated solid oxide comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 55. The process defined in any one of aspects 1-46, wherein the chemically-treated solid oxide comprises a fluorided solid oxide, a sulfated solid oxide, or a combination thereof.

Aspect 56. The process defined in any one of aspects 1-46, wherein the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Aspect 57. The process defined in any one of aspects 1-46, wherein the chemically-treated solid oxide comprises fluorided silica-coated alumina.

Aspect 58. The process defined in any one of aspects 1-46, wherein the chemically-treated solid oxide comprises sulfated alumina.

Aspect 59. The process defined in any one of the preceding aspects, wherein the catalyst composition comprises a co-catalyst, e.g., any co-catalyst disclosed herein.

Aspect 60. The process defined in any one of the preceding aspects, wherein the co-catalyst comprises an organoaluminum compound, an organozinc compound, an organomagnesium compound, an organolithium compound, or any combination thereof.

Aspect 61. The process defined in any one of the preceding aspects, wherein the co-catalyst comprises an organoaluminum compound.

Aspect 62. The process defined in aspect 61, wherein the organoaluminum compound comprises any organoaluminum compound disclosed herein, e.g., trimethylaluminum, triethylaluminum, triisobutylaluminum, etc., or combinations thereof.

Aspect 63. The process defined in any one of aspects 1-62, wherein the catalyst composition is substantially free of aluminoxane compounds, organoboron or organoborate compounds, ionizing ionic compounds, or combinations thereof.

Aspect 64. The process defined in any one of aspects 1-62, wherein the co-catalyst comprises an aluminoxane compound, an organoboron or organoborate compound, an ionizing ionic compound, an organoaluminum compound, an organozinc compound, an organomagnesium compound, an organolithium compound, or any combination thereof.

Aspect 65. The process defined in any one of the preceding aspects, wherein the catalyst composition is produced by a process comprising contacting, in any order, catalyst component I, catalyst component II, the chemically-treated solid oxide, and the co-catalyst (if utilized).

Aspect 66. The process defined in any one of the preceding aspects, wherein a weight ratio of the chemically-treated solid oxide to the total of catalyst component I and catalyst component II in any range of weight ratios disclosed herein, e.g., from about 50:1 to about 1500:1, from about 50:1 to about 1000:1, from about 50:1 to about 800:1, from about 60:1 to about 800:1, from about 60:1 to about 600:1, from about 70:1 to about 600:1, from about 70:1 to about 500:1, etc.

Aspect 67. The process defined in any one of the preceding aspects, wherein a molar ratio of the co-catalyst to the total of catalyst component I and catalyst component II is in any range of molar ratios disclosed herein, e.g., from about 5:1 to about 5000:1, from about 5:1 to about 1000:1, from about 5:1 to about 250:1, from about 10:1 to about 150:1, etc.

Aspect 68. The process defined in any one of the preceding aspects, wherein a molar ratio of propylene to the total of catalyst component I and catalyst component II is in any range of molar ratios disclosed herein, e.g., from about $1 \times 10^3:1$ to about $1 \times 10^9:1$, from about $5 \times 10^3:1$ to about $1 \times 10^9:1$, from about $5 \times 10^3:1$ to about $5 \times 10^8:1$, from about $1 \times 10^4:1$ to about $1 \times 10^8:1$, from about $5 \times 10^4:1$ to about $1 \times 10^8:1$, from about $5 \times 10^4:1$ to about $5 \times 10^7:1$, from about $1 \times 10^5:1$ to about $5 \times 10^7:1$, from about $1 \times 10^5:1$ to about $1 \times 10^5:1$, from about $1 \times 10^7:1$ to about $1 \times 10^5:1$ to about $5 \times 10^6:1$, from about $1 \times 10^5:1$ to about $1 \times 10^6:1$, etc.

Aspect 69. The process defined in any one of the preceding aspects, wherein a composition comprising the olefin feedstock is any suitable composition, e.g., refinery grade propylene, chemical grade propylene, polymer grade propylene, etc., or a composition comprising the olefin feedstock comprises any suitable amount of propylene, $C_1$ to $C_{4+}$ paraffins, and $C_2$ and/or $C_{4+}$ olefins disclosed herein.

Aspect 70. The process defined in any one of the preceding aspects, wherein the oligomerization conditions comprise an oligomerization temperature in any oligomerization temperature range disclosed herein, e.g., from about 0° C. to about 165° C., from about 20° C. to about 160° C., from about 40° C. to about 160° C., from about 50° C. to about 150° C., from about 50° C. to about 140° C., from about 50° C. to about 130° C., from about 60° C. to about 130° C., from about 60° C. to about 120° C., etc.

Aspect 71. The process defined in any one of the preceding aspects, wherein the oligomerization conditions comprise a reaction pressure (or propylene partial pressure) in any range disclosed herein, e.g., from about 50 psig (344 KPa) to about 4,000 psig (27.6 MPa), from about 100 psig (689 KPa) to about 3,000 psig (20.9 MPa), from about 200 psig (1.4 MPa) to about 2,000 psig (13.8 MPa), from about 250 psig (1.5 MPa) to about 1,500 psig (10.3 MPa), etc.

Aspect 72. The process defined in any one of the preceding aspects, wherein the oligomer product is formed in the presence of hydrogen.

Aspect 73. The process defined in aspect 72, wherein the oligomer product is formed at a hydrogen partial pressure in any range disclosed herein, e.g., from about 1 psig (6.9 kPa) to about 2000 psig (13.8 MPa), from about 5 psig (34 kPa) to about 1500 psig (10.3 MPa), from about 10 psig (69 kPa) to about 1000 psig (6.9 MPa), from about 10 psig (69 kPa) to about 500 psig (3.5 MPa), from about 25 psig (172 kPa) to about 500 psig (3.4 MPa), etc.

Aspect 74. The process defined in any one of aspects 1-71, wherein the oligomer product is formed in the substantial absence of hydrogen (e.g., no added hydrogen).

Aspect 75. The process defined in any one of the preceding aspects, wherein the activity of the catalyst composition is at least about 25,000, 30,000, 35,000, or 40,000 grams of oligomer product per gram of total catalyst component I and catalyst component II per hour.

Aspect 76. The process defined in any one of the preceding aspects, wherein the oligomer product is formed in a reaction system comprising a fixed bed reactor, a stirred tank reactor, a plug flow reactor, a loop slurry reactor, or a combination thereof.

Aspect 77. The process defined in any one of the preceding aspects, wherein the process further comprises a step of deactivating the catalyst composition using any suitable technique or any technique disclosed herein.

Aspect 78. The process defined in any one of the preceding aspects, wherein the process further comprises a step of separating unreacted monomer (e.g., propylene) and the oligomer product from the catalyst composition or deactivated catalyst composition using any suitable technique or any technique disclosed herein, e.g., filtration, etc.

Aspect 79. The process defined in any one of the preceding aspects, wherein the process further comprises isolating a heavy propylene oligomer by a step of removing unreacted propylene and at least a portion of the light propylene oligomers (e.g., $C_6$-$C_{12}$, etc.) from the oligomer product using any suitable technique or any technique disclosed herein, e.g., flash processes, distillations processes, as well as combinations thereof.

Aspect 80. The process defined in aspect 79, wherein the flash point of the heavy propylene oligomer is greater than that of a heavy propylene oligomer prepared using the same catalyst composition without catalyst component I and greater than that of a heavy propylene oligomer prepared using the same catalyst composition without catalyst component II, under the same processing conditions.

Aspect 81. The process defined in any one of the preceding aspects, wherein the process further comprises a step of hydrogenating the oligomer product or the heavy propylene oligomer using any suitable technique or any technique disclosed herein.

Aspect 82. The process defined in aspect 81, wherein the flash point of the hydrogenated heavy propylene oligomer is greater than that of a hydrogenated heavy propylene oligomer prepared using the same catalyst composition without catalyst component I and greater than that of a hydrogenated heavy propylene oligomer prepared using the same catalyst composition without catalyst component II, under the same processing conditions.

Aspect 83. The process defined in any one of aspects 79-82, wherein the heavy propylene oligomer (or the hydrogenated heavy propylene oligomer) has a flash point in any range of flash points disclosed herein, e.g., from about 140 to about 300° C., from about 140 to about 260° C., from about 160 to about 240° C., from about 160 to about 200° C., etc.

Aspect 84. The process defined in any one of aspects 79-83, wherein the heavy propylene oligomer (or the hydrogenated heavy propylene oligomer) has a Mn in any range of Mn's disclosed herein, e.g., from about 250 to about 5000 g/mol, from about 500 to about 5000 g/mol, from about 500 to about 4000 g/mol, from about 500 to about 2500 g/mol, from about 600 to about 2500 g/mol, from about 750 to about 2500 g/mol, etc.

Aspect 85. The process defined in any one of aspects 79-84, wherein the heavy propylene oligomer (or the hydrogenated heavy propylene oligomer) has a pour point in any range of pour points disclosed herein, e.g., from about 0 to about −55° C., from about 0 to about −45° C., from about 0 to about −30° C., from about −5 to about −45° C., from about −5 to about −30° C., from about −10 to about −40° C., from about −10 to about −30° C., etc.

Aspect 86. The process defined in any one of aspects 79-85, wherein the heavy propylene oligomer (or the hydrogenated heavy propylene oligomer) has a viscosity index in any range of viscosity indices disclosed herein, e.g., from about 75 to about 200, from about 75 to about 175, from about 80 to about 175, from about 80 to about 150, from about 80 to about 130, from about 90 to about 150, from about 90 to about 130, from about 100 to about 130, etc.

Aspect 87. The process defined in any one of aspects 79-86, wherein the heavy propylene oligomer (or the hydrogenated heavy propylene oligomer) has a Mw in any range of Mw's disclosed herein, e.g., from about 500 to about 10,000 g/mol, from about 750 to about 7000 g/mol, from about 1000 to about 5000 g/mol, from about 500 to about 4000 g/mol, from about 500 to about 3000 g/mol, from about 1000 to about 5000 g/mol, from about 1500 to about 5000 g/mol, etc.

Aspect 88. The process defined in any one of aspects 79-87, wherein the heavy propylene oligomer (or the hydrogenated heavy propylene oligomer) has a ratio of Mw/Mn in any range of Mw/Mn ratios disclosed herein, e.g., from about 1.6 to about 5, from about 1.8 to about 5, from about 1.8 to about 4.5, from about 1.9 to about 4, from about 2 to about 4, etc.

Aspect 89. The process defined in any one of aspects 79-88, wherein the heavy propylene oligomer (or the hydrogenated heavy propylene oligomer) has a ratio of Mz/Mw in any range of Mz/Mw ratios disclosed herein, e.g., from about 1.9 to about 8, from about 1.9 to about 6, from about 1.9 to about 5, from about 1.9 to about 3, etc.

Aspect 90. The process defined in any one of aspects 79-89, wherein the heavy propylene oligomer (or the hydrogenated heavy propylene oligomer) has a kinematic viscosity at 100° C. in any range of kinematic viscosities at 100° C. disclosed herein, e.g., from about 6 to about 200 cSt, from about 8 to about 150 cSt, from about 10 to about 150 cSt, from about 10 to about 100 cSt, from about 12 to about 150 cSt, from about 12 to about 100 cSt, from about 12 to about 80 cSt, from about 12 to about 60 cSt, from about 14 to about 50 cSt, etc.

Aspect 91. The process defined in any one of aspects 79-90, wherein the heavy propylene oligomer (or the hydrogenated heavy propylene oligomer) has a kinematic viscosity at 40° C. in any range of kinematic viscosities at 40° C. disclosed herein, e.g., from about 25 to about 8000 cSt, from about 50 to about 6000 cSt, from about 75 to about 6000 cSt, from about 75 to about 400 cSt, from about 25 to about 800 cSt, about 100 to about 6000 cSt, from about 100 to about 4000 cSt, from about 150 to about 6000, from about 150 to about 400 cSt, from about 150 to about 2000 cSt, from about 175 to about 2000 cSt, from about 175 to about 1500 cSt, from about 200 to about 2000 cSt, from about 200 to about 1500 cSt, from about 200 to about 800 cSt, etc.

Aspect 92. A heavy propylene oligomer or hydrogenated heavy propylene oligomer produced by the process defined in any one of aspects 79-91.

Aspect 93. A composition comprising the heavy propylene oligomer or hydrogenated heavy propylene oligomer defined in aspect 92.

Aspect 94. A base oil comprising the heavy propylene oligomer or hydrogenated heavy propylene oligomer defined in aspect 92.

Aspect 95. A lubricant composition comprising the heavy propylene oligomer or hydrogenated heavy propylene oligomer defined in aspect 92, or the base oil defined in aspect 94.

Aspect 96. The lubricant composition defined in aspect 95, further comprising any suitable additive or any additive disclosed herein, as well as combinations thereof.

We claim:

1. An oligomerization process comprising:
   contacting an olefin feedstock comprising propylene with a catalyst composition comprising:
   (i) catalyst component I comprising an unbridged zirconium or hafnium based metallocene compound containing two cyclopentadienyl groups, two indenyl groups, or a cyclopentadienyl and an indenyl group;
   (ii) catalyst component II comprising a single atom bridged, zirconium or hafnium based metallocene compound containing two cyclopentadienyl groups;
   (iii) a chemically-treated solid oxide; and
   (iv) optionally, a co-catalyst;
   to form an oligomer product under oligomerization conditions; and
   isolating a heavy propylene oligomer by removing unreacted propylene and at least a portion of light propylene oligomers from the oligomer product using one or more separation steps, wherein the heavy propylene oligomer is characterized by a pour point in a range from about 0 to about −55° C.

2. The process of claim 1, wherein the heavy propylene oligomer is characterized by:
   a flash point in a range from about 140 to about 300° C.; and
   a viscosity index in a range from about 75 to about 200.

3. The process of claim 1, wherein the heavy propylene oligomer is characterized by:
   a flash point in a range from about 140 to about 260° C.;
   a viscosity index in a range from about 80 to about 130; and
   a pour point in a range from about −5 to about −30° C.

4. The process of claim 1, wherein the heavy propylene oligomer is characterized by:
   a Mw in a range from about 1500 to about 5000 g/mol;
   a ratio of Mw/Mn in a range from about 1.8 to about 4.5;
   a ratio of Mz/Mw in a range from about 1.9 to about 5;
   a kinematic viscosity at 40° C. in a range from about 200 to about 1500 cSt; and
   a kinematic viscosity at 100° C. in a range from about 14 to about 50 cSt.

5. The process of claim 1, wherein a flash point of the heavy propylene oligomer is greater than that of a heavy propylene oligomer prepared using the same catalyst composition without catalyst component I, and greater than that of a heavy propylene oligomer prepared using the same catalyst composition without catalyst component II, under the same processing conditions.

6. The process of claim 1, wherein the olefin feedstock comprising propylene is contacted with the catalyst composition in the presence of hydrogen.

7. The process of claim 1, wherein:
   the catalyst composition comprises a co-catalyst; and
   the chemically-treated solid oxide comprises a fluorided solid oxide and/or a sulfated solid oxide.

8. The process of claim 1, wherein catalyst component I comprises an unbridged metallocene compound having formula (I):

wherein:
   $M^1$ is Zr or Hf;
   $Cp^A$ and $Cp^B$ independently are a cyclopentadienyl group or an indenyl group; and
   each X independently is a monoanionic ligand.

9. The process of claim 8, wherein:
   $M^1$ is Zr;
   $Cp^A$ and $Cp^B$ independently are a cyclopentadienyl group or an indenyl group, either unsubstituted or with one $C_1$ to $C_{18}$ hydrocarbyl substituent; and
   each X is Cl.

10. The process of claim 1, wherein catalyst component II comprises a bridged metallocene compound having formula (II):

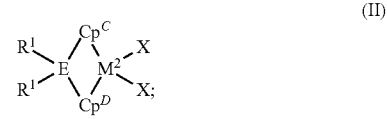

wherein:
M² is Zr or Hf;
Cp^C and Cp^D independently are a cyclopentadienyl group;
E is C or Si;
each R¹ independently is H or a $C_1$ to $C_{18}$ hydrocarbyl group; and
each X independently is a monoanionic ligand.

11. The process of claim 10, wherein:
M² is Zr;
Cp^C and $C_p^D$ independently are a cyclopentadienyl group, either unsubstituted or with one $C_1$ to $C_{18}$ hydrocarbyl substituent;
each 10 independently is a phenyl group, a $C_1$ to $C_8$ alkyl group, or a $C_3$ to $C_8$ alkenyl group; and
each X independently is a halide or $C_1$ to $C_{18}$ hydrocarbyl or hydrocarbylaminyl group.

12. The process of claim 1, wherein:
the chemically-treated solid oxide comprises a solid oxide treated with an electron-withdrawing anion, and wherein the solid oxide comprises silica, alumina, silica-alumina, silica-coated alumina, or a combination thereof; and the electron-withdrawing anion comprises sulfate, fluoride, chloride, or a combination thereof; and
a weight ratio of catalyst component I to catalyst component II is in a range from about 2:1 to about 1:2.

13. The process of claim 1, wherein:
the oligomer product is formed in a reaction system comprising a fixed bed reactor, a stirred tank reactor, a plug flow reactor, a loop slurry reactor, or a combination thereof; and
an activity of the catalyst composition is at least about 25,000 grams of the oligomer product per gram of catalyst component I and catalyst component II per hour.

14. The process of claim 1, wherein the catalyst composition comprises a co-catalyst, and wherein the co-catalyst comprises an organoaluminum compound.

15. The process of claim 14, wherein the chemically-treated solid oxide comprises fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

16. The process of claim 14, wherein:
catalyst component I comprises an unbridged metallocene compound having formula (I):

and
catalyst component II comprises a bridged metallocene compound having formula (II):

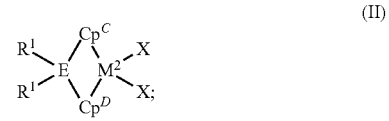

wherein:
M¹ and M² are Zr;
Cp^A and Cp^B independently are a cyclopentadienyl group or an indenyl group;
Cp^C and Cp^D independently are a cyclopentadienyl group;
E is C or Si;
each R¹ independently is H or a $C_1$ to $C_{18}$ hydrocarbyl group; and
each X independently is a monoanionic ligand.

17. The process of claim 16, wherein the heavy propylene oligomer comprises at least about 98 mol % propylene units.

18. The process of claim 16, wherein the process further comprises a step of hydrogenating the heavy propylene oligomer to produce a hydrogenated heavy propylene oligomer.

19. The process of claim 18, wherein a flash point of the hydrogenated heavy propylene oligomer is greater than that of a hydrogenated heavy propylene oligomer prepared using the same catalyst composition without catalyst component I, and greater than that of a hydrogenated heavy propylene oligomer prepared using the same catalyst composition without catalyst component II, under the same processing conditions.

20. The process of claim 18, wherein the hydrogenated heavy propylene oligomer is characterized by:
a flash point in a range from about 140 to about 260° C.;
a viscosity index in a range from about 80 to about 130;
a pour point in a range from about −5 to about −30° C.;
a kinematic viscosity at 40° C. in a range from about 200 to about 1500 cSt; and
a kinematic viscosity at 100° C. in a range from about 10 to about 100 cSt.

* * * * *